(12) United States Patent
Felder et al.

(10) Patent No.: US 10,758,298 B2
(45) Date of Patent: Sep. 1, 2020

(54) ARTICULATING ELECTROSURGICAL TOOLS

(71) Applicant: Ethicon LLC, Guaynabo, PR (US)

(72) Inventors: Kevin D. Felder, Cincinnati, OH (US); Mary T. Carter, Boston, MA (US); Michel G. Bruehwiler, Newton, MA (US); Cole Constantineau, Cambridge, MA (US); Jeffrey Chagnon, Somerville, MA (US); Daniel J. Yasevac, Arlington, MA (US); Kevin DelSignore, Brighton, MA (US); Veaceslav G. Arabagi, Cambridge, MA (US)

(73) Assignee: Ethicon LLC, Guaynabo, PR (US)

( * ) Notice: Subject to any disclaimer, the term of this patent is extended or adjusted under 35 U.S.C. 154(b) by 398 days.

(21) Appl. No.: 15/411,411

(22) Filed: Jan. 20, 2017

(65) Prior Publication Data
US 2018/0206904 A1 Jul. 26, 2018

(51) Int. Cl.
*A61B 18/12* (2006.01)
*A61B 18/14* (2006.01)
(Continued)

(52) U.S. Cl.
CPC .......... *A61B 18/1445* (2013.01); *A61B 34/30* (2016.02); *A61B 34/71* (2016.02);
(Continued)

(58) Field of Classification Search
CPC ...... A61B 18/1445; A61B 2018/00595; A61B 2018/1455; A61B 34/30; A61B 34/35;
(Continued)

(56) References Cited

U.S. PATENT DOCUMENTS 4,763,669 A * 8/1988 Jaeger ................ A61B 10/0291
30/251
5,275,615 A * 1/1994 Rose ...................... A61B 17/29
606/207
(Continued)

FOREIGN PATENT DOCUMENTS

WO WO-2014039054 A1 3/2014
WO WO-2014151621 A1 9/2014
(Continued)

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Daniel W Fowler
(74) *Attorney, Agent, or Firm* — Mintz Levin Cohn Ferris Glovsky and Popeo, P.C.

(57) ABSTRACT

Various exemplary systems, devices, and methods for articulating electrosurgical tools are provided. In general, a surgical tool can be configured to articulate in two planes by selectively pivoting at first and second joints of the surgical tool. The surgical tool can include a plurality of cables configured to facilitate the articulation. Each of the cables can be configured to flex or bend at the first and second joints and can be configured to be selectively actuated to cause the pivoting at the first and second joints. The surgical tool can be configured to releasably couple to a robotic surgical system configured to control a variety of movements and actions associated with the surgical tool, such as the pivoting at the first and second joints.

16 Claims, 25 Drawing Sheets

(51) Int. Cl.
    *A61B 34/30*     (2016.01)
    *A61B 34/00*     (2016.01)
    *A61B 46/10*     (2016.01)
    *A61B 17/29*     (2006.01)
    *A61B 34/35*     (2016.01)
    *A61B 18/00*     (2006.01)

(52) U.S. Cl.
CPC .............. *A61B 46/10* (2016.02); *A61B 34/35* (2016.02); *A61B 34/74* (2016.02); *A61B 2017/2908* (2013.01); *A61B 2017/2927* (2013.01); *A61B 2017/2932* (2013.01); *A61B 2018/00595* (2013.01); *A61B 2018/1455* (2013.01); *A61B 2034/306* (2016.02); *A61B 2034/715* (2016.02); *A61B 2034/741* (2016.02); *A61B 2034/742* (2016.02)

(58) Field of Classification Search
CPC ... A61B 34/71; A61B 34/74; A61B 2034/306; A61B 2034/715; A61B 2034/741
See application file for complete search history.

(56) References Cited

U.S. PATENT DOCUMENTS

| | | | | |
|---|---|---|---|---|
| 5,419,339 | A * | 5/1995 | Palmer | A61B 10/06 |
| | | | | 600/564 |
| 5,454,827 | A * | 10/1995 | Aust | A61B 17/29 |
| | | | | 600/564 |
| 5,766,196 | A * | 6/1998 | Griffiths | A61B 17/29 |
| | | | | 600/564 |
| 5,928,163 | A * | 7/1999 | Roberts | A61B 18/1445 |
| | | | | 600/567 |
| 6,077,287 | A * | 6/2000 | Taylor | A61B 17/1608 |
| | | | | 606/170 |
| 8,771,270 | B2 | 7/2014 | Burbank | |
| 9,055,961 | B2 | 6/2015 | Manzo et al. | |
| 9,220,559 | B2 * | 12/2015 | Worrell | A61B 18/1445 |
| 2002/0123667 | A1 * | 9/2002 | Ouchi | A61B 18/1445 |
| | | | | 600/201 |
| 2005/0096694 | A1 * | 5/2005 | Lee | A61B 17/00234 |
| | | | | 606/205 |
| 2011/0213360 | A1 * | 9/2011 | Cunningham | A61B 17/29 |
| | | | | 606/41 |
| 2011/0251608 | A1 * | 10/2011 | Timm | A61B 17/295 |
| | | | | 606/41 |
| 2012/0109186 | A1 * | 5/2012 | Parrott | A61B 17/29 |
| | | | | 606/206 |
| 2013/0131651 | A1 | 5/2013 | Strobl et al. | |
| 2014/0148806 | A1 | 5/2014 | Witt et al. | |
| 2014/0200610 | A1 * | 7/2014 | Igov | A61B 17/2909 |
| | | | | 606/205 |
| 2015/0305797 | A1 * | 10/2015 | Hassoun | A61B 17/29 |
| | | | | 606/27 |

FOREIGN PATENT DOCUMENTS

| | | |
|---|---|---|
| WO | WO-2014151952 A1 | 9/2014 |
| WO | WO-2014173409 A1 | 10/2014 |
| WO | WO-2017155931 A1 | 9/2017 |

OTHER PUBLICATIONS

U.S. Appl. No. 15/237,648 entitled "Methods, Systems, and Devices for Causing End Effector Motion With a Robotic Surgical System" filed Aug. 16, 2016.
U.S. Appl. No. 15/237,653 entitled "Methods, Systems, and Devices for Controlling a Motor of a Robotic Surgical Systems" filed Aug. 16, 2016.
U.S. Appl. No. 15/371,764 entitled "Surgical Tool Wrists" filed Dec. 7, 2016.
International Search Report and Written Opinion for International App. No. PCT/IB2018/050205 dated Mar. 8, 2018 (14 pages).
U.S. Appl. No. 15/451,483 entitled "Robotic Bi-Polar Instruments" filed Mar. 7, 2017.

* cited by examiner

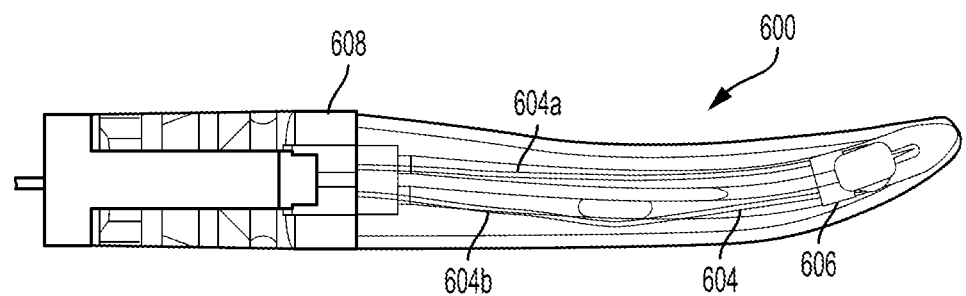
FIG. 35
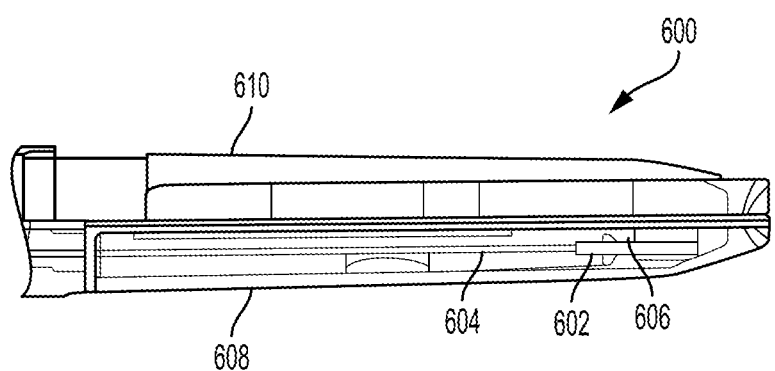
FIG. 36
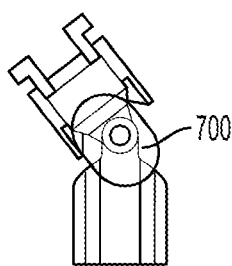 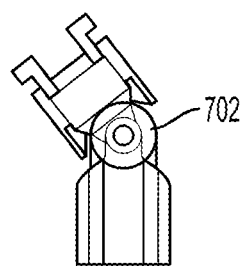 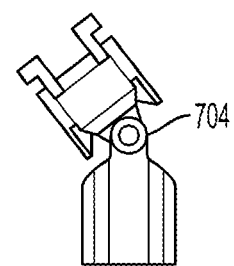
FIG. 37　　　FIG. 38　　　FIG. 39

ARTICULATING ELECTROSURGICAL TOOLS

FIELD

Methods and devices are provided for robotic surgery, and in particular articulating electrosurgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, systems, devices, and methods for articulating electrosurgical tools are provided.

In one aspect, a surgical device is provided that in one embodiment includes an elongate shaft, and an end effector configured to engage tissue and apply energy thereto. The end effector is configured to selectively articulate at an angle relative to a longitudinal axis of the elongate shaft along a first plane and along a second plane that is transverse to the second plane. The surgical device also includes a linkage located between a proximal end of the end effector and a distal end of the end effector, a first pair of articulation cables each extending across the linkage, and a second pair of articulation cables each extending across the linkage. The first pair of articulation cables is configured to be selectively actuated to cause the pivoting of the linkage and thereby cause the articulation of the end effector along a first plane. The linkage is limited to pivoting relative to the elongate shaft along the first plane. The second pair of articulation cables is configured to be selectively actuated to cause articulation of the end effector along a second plane, and the end effector is limited to pivoting relative to the linkage along the second plane.

The surgical device can vary in any number of ways. For example, each of the articulation cables can be offset from the first plane and the second plane. For another example, each of the articulation cables can be in one of first plane and the second plane.

For yet another example, the surgical device can include a cutting element configured to move longitudinally along the end effector to cut tissue engaged by the end effector, and a cutting element cable extending along the linkage and being configured to be actuated to cause the movement of the cutting element. In at least some embodiments, the cutting element cable can be configured to be pushed distally to cause the movement of the cutting element. In at least some embodiments, the cutting element cable can be operatively coupled to a pulley at a distal end of the end effector.

For still another example, the surgical device can include a closure cable extending along the linkage and being configured to be actuated to selectively cause opening of the end effector and closing of the end effector. In at least some embodiments, the closure cable can be configured to be pushed distally to cause the opening of the end effector and closing of the end effector, the closure cable can extend coaxially with a longitudinal axis of the elongate shaft, the closure cable can include a pair of cables arranged radially around a longitudinal axis of the elongate shaft, and/or the surgical device can include a cutting element configured to move longitudinally along the end effector to cut tissue engaged by the end effector and can include a cutting element cable extending along the linkage and being configured to be actuated to cause the movement of the cutting element.

For another example, the actuation of the articulation cables can be configured to be controlled by a robotic surgical system.

In another embodiment, a surgical device is provided that includes an elongate shaft, and an end effector configured to engage tissue, configured to apply energy to the tissue, and configured to selectively articulate at an angle relative to a longitudinal axis of the elongate shaft along a first plane and along a second plane that is transverse to the second plane. The end effector includes a pair of jaws configured to move between open and closed positions. The surgical device also includes a first pair of articulation cables extending along the elongate shaft offset from and substantially parallel to a longitudinal axis of the elongate shaft, a second pair of articulation cables extending along the elongate shaft offset from and substantially parallel to the longitudinal axis of the elongate shaft, and a pair of closure cables extending along the elongate shaft and substantially parallel to the longitudinal axis of the elongate shaft. The first pair of articulation cables is configured to be actuated to articulate the end effector in only yaw movement relative to the elongate shaft. The second pair of articulation cables is configured to be actuated to articulate the end effector in only pitch movement relative to the elongate shaft. The pair of closure cables is configured to be actuated to move the pair of jaws between the open and closed positions.

The surgical device can have any number of variations. For example, the first pair of articulation cables can be configured to be actuated without the second pair of articulation cables being actuated such that the end effector articulates in only yaw movement, the second pair of articulation cables can be configured to be actuated without the first pair of articulation cables being actuated such that the end effector articulates in only pitch movement, and the first and second pairs of articulation cables can be configured to be actuated such that the end effector articulates in pitch movement and yaw movement.

For another example, the surgical device can include a cutting element configured to move longitudinally along the end effector to cut tissue engaged by the end effector, the surgical device can include a cutting element cable extending along the elongate shaft and substantially parallel to the longitudinal axis of the elongate shaft, and the cutting element cable can be configured to be actuated to cause the movement of the cutting element. In at least some embodiments, the cutting element cable can be configured to be pushed distally to cause the movement of the cutting element. In at least some embodiments, the cutting element cable can be operatively coupled to a pulley at a distal end of the end effector.

For yet another example, the actuation of the first and second pairs of articulation cables and the actuation of the pair of closure cables can each be configured to be controlled by a robotic surgical system.

In another aspect, a surgical method is provided that in one embodiment includes advancing an end effector at a distal end of a surgical tool into a patient, causing a plurality of articulation cables that extend along the elongate shaft to each bend at a first pivot joint about a first axis to thereby cause articulation of the end effector about the first axis relative to an elongate shaft of the surgical tool, and causing the plurality of articulation cables to each bend at a second pivot joint about a second axis to thereby cause articulation of the end effector about the second axis relative to an elongate shaft of the surgical tool. The surgical tool is configured to apply energy to tissue engaged by the end effector. The first axis is substantially perpendicular to the second axis, and the articulation cables are configured to be bent about the first axis and the second axis such that the end effector is articulated about each of the first and second axes.

The surgical method can vary in any number of ways. For example, the surgical method can include engaging tissue with the end effector, the surgical method can include actuating a cutting element cable that extends along the elongate shaft to thereby cause a cutting element to translate along the end effector and cut the tissue, and the cutting element cable can be configured to be bent at the first pivot joint about the first axis and bent at the second pivot joint about the second axis. For another example, the surgical method can include actuating a closure cable that extends along the elongate shaft to thereby cause the end effector to at least one move from an open position to a closed position and move from the closed position to the open position, and the closure cable can be configured to be bent at the first pivot joint about the first axis and bent at the second pivot joint about the second axis. For yet another example, the surgical tool can be operatively coupled to a robotic surgical system, and the robotic surgical system can be configured to cause the plurality of articulation cables to be bent at the first pivot joint and to be bent at the second pivot joint.

BRIEF DESCRIPTION OF THE DRAWINGS

The invention will be more fully understood from the following detailed description taken in conjunction with the accompanying drawings, in which:

FIG. 35 is another top, partially transparent view of the distal portion of the surgical tool of FIG. 33 with a cutting element thereof advanced to a distal-most position;

FIG. 36 is a side, partially transparent view of the distal portion of the surgical tool of FIG. 35;

FIG. 37 is a side, partially transparent view of an intermediate portion of another embodiment of a surgical tool;

FIG. 38 is a side, partially transparent view of an intermediate portion of yet another embodiment of a surgical tool;

FIG. 39 is a side, partially transparent view of an intermediate portion of still another embodiment of a surgical tool;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary systems, devices, and methods for articulating electrosurgical tools are provided. In general, a surgical tool can be configured to articulate in two planes by selectively pivoting at first and second joints of the surgical tool. The surgical tool can include a plurality of cables configured to facilitate the articulation. Each of the cables can be configured to flex or bend at the first and second joints and can be configured to be selectively actuated to cause the pivoting at the first and second joints. The surgical tool can be configured to releasably couple to a robotic surgical system (also referred to herein as a "surgical robot") configured to control a variety of movements and actions associated with the surgical tool, such as the pivoting at the first and second joints.

Figure 1:
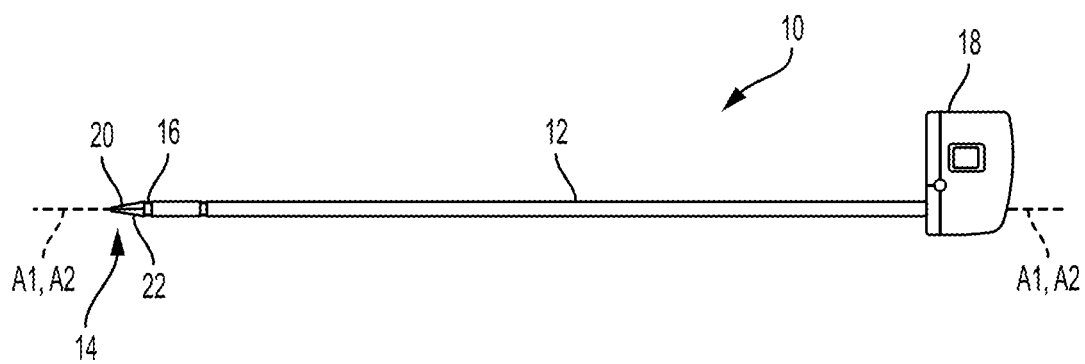
FIG. 1 is a side schematic view of one embodiment of a surgical tool.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. Pat. No. 9,055,961 entitled "Fusing And Cutting Surgical Instrument And Related Methods" filed on Feb. 17, 2012, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

Figure 2:
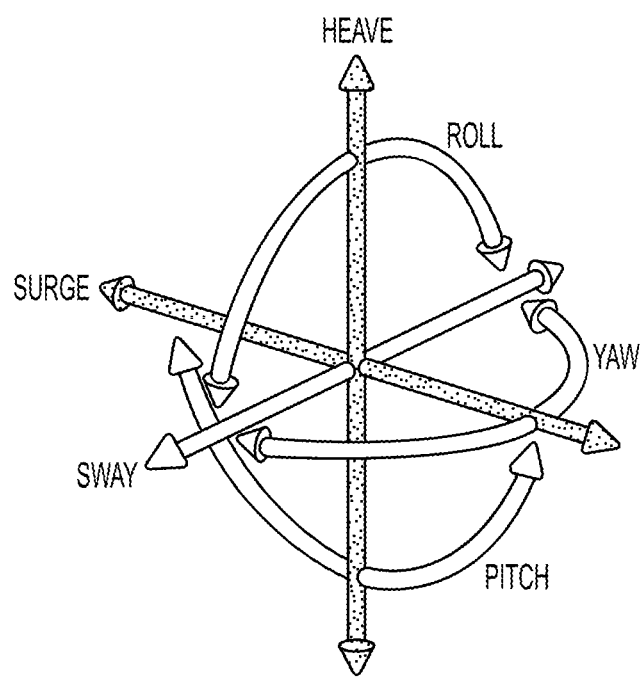
FIG. 2 is a graphical representation of terminology associated with six degrees of freedom.

FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The movement of the end effector 14 in this illustrated embodiment includes articulating movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1. The movement of the end effector 14 in this illustrated embodiment also includes rotational movement of the end effector 14 in which the end effector 14 rotates about its longitudinal axis A2, either with or without corresponding rotation of the shaft 12 about its longitudinal axis A1.

The surgical tool 10 can include one or more actuation shafts configured to facilitate movement of the end effector 14. Each of the one or more actuation shafts can extend along the shaft 12 (e.g., in an inner lumen thereof) and can be operatively coupled to the housing 18 and to the end effector 14. In this way, a tool driver coupled to the housing 18 can be configured to provide input to the surgical tool 10 via the tool housing 18 and thereby actuate the one or more actuation shafts to cause movement of the end effector 14.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 3:
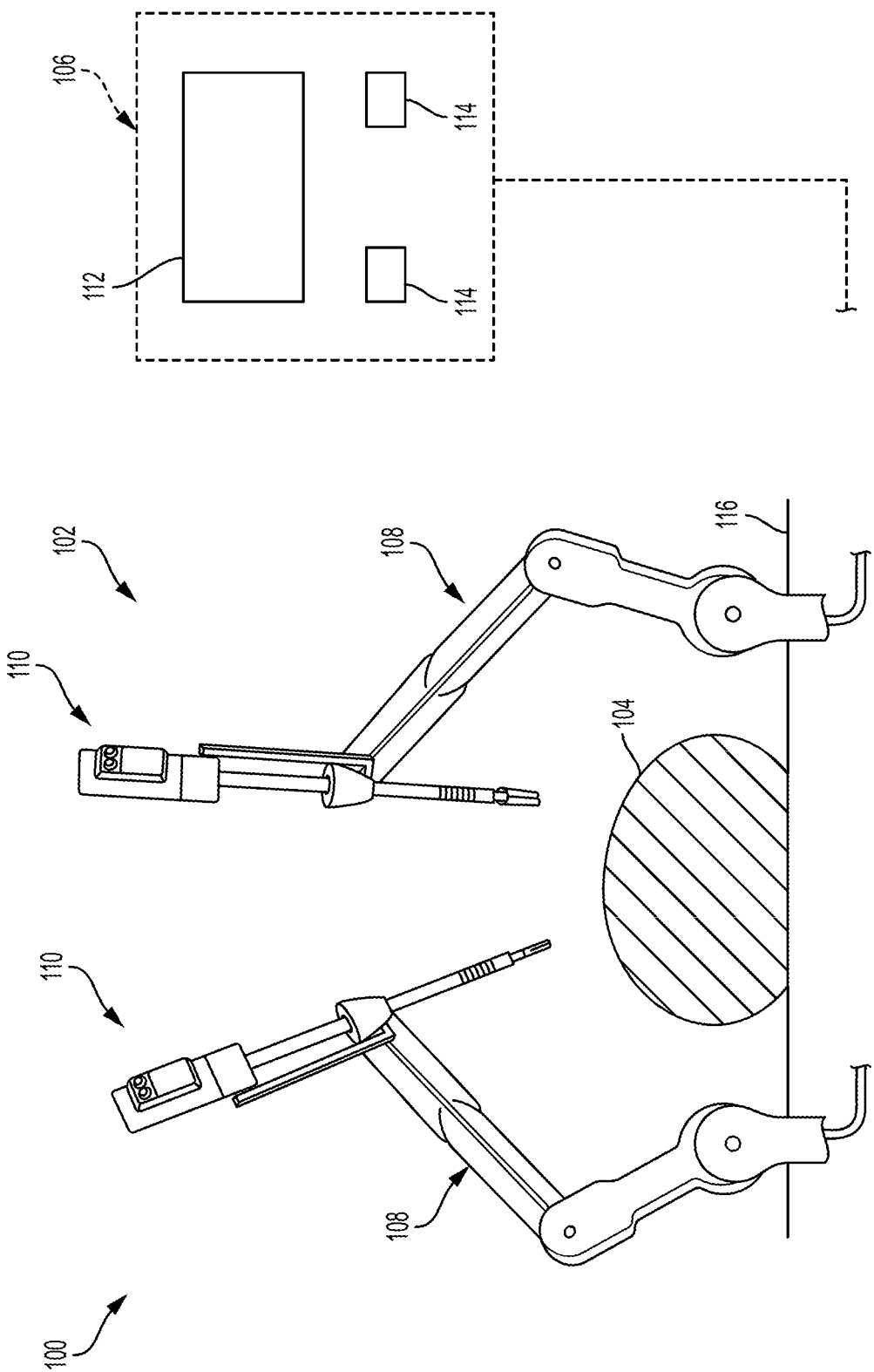
FIG. 3 is a perspective view of one embodiment of a robotic surgical system that includes a patient-side portion and a user-side portion.

FIG. 3 is a perspective view of one embodiment of a robotic surgical system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 3, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 3). Alternatively, the patient-side portion 102 can include a single assembly that includes one or more robotic arms 108 extending therefrom.

Figure 4:
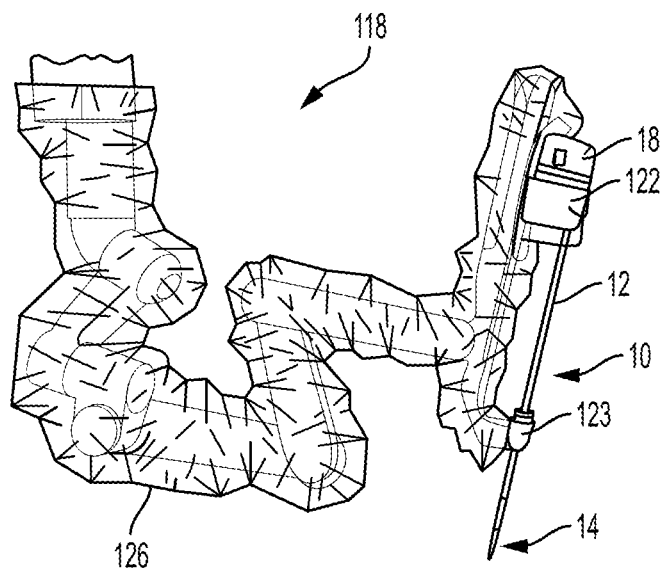
FIG. 4 is a perspective view of one embodiment of a robotic arm of a robotic surgical system with the surgical tool of FIG. 1 releasably and replaceably coupled to the robotic arm.

FIG. 4 illustrates another embodiment of a robotic arm 118 and the surgical tool 10 of FIG. 1 releasably and replaceably coupled to the robotic arm 118. Other surgical instruments can instead be coupled to the arm 118, as discussed herein. The robotic arm 118 is configured to support and move the associated tool 10 along one or more degrees of freedom (e.g., all six Cartesian degrees of freedom, five or fewer Cartesian degrees of freedom, etc.).

The robotic arm 118 can include a tool driver 122 at a distal end of the robotic arm 118, which can assist with controlling features associated with the tool 10. The robotic arm 118 can also include an entry guide 123 (e.g., a cannula mount, cannula, etc.) that can be a part of or releasably and replaceably coupled to the robotic arm 118, as shown in FIG. 4. A shaft of a tool assembly can be inserted through the entry guide 123 for insertion into a patient, as shown in FIG. 4 in which the shaft 12 of the tool 10 of FIG. 1 is shown inserted through the entry guide 123.

In order to provide a sterile operation area while using the surgical system, a barrier 126 can be placed between the actuating portion of the surgical system (e.g., the robotic arm 118) and the surgical instruments coupled thereto (e.g., the tool 10, etc.). A sterile component, such as an instrument sterile adapter (ISA), can also be placed at the connecting interface between the tool 10 and the robotic arm 118. The placement of an ISA between the tool 10 and the robotic arm 108 can ensure a sterile coupling point for the tool 10 and the robotic arm 118. This permits removal of surgical instruments from the robotic arm 118 to exchange with other surgical instruments during the course of a surgery without compromising the sterile surgical field.

Figure 5:
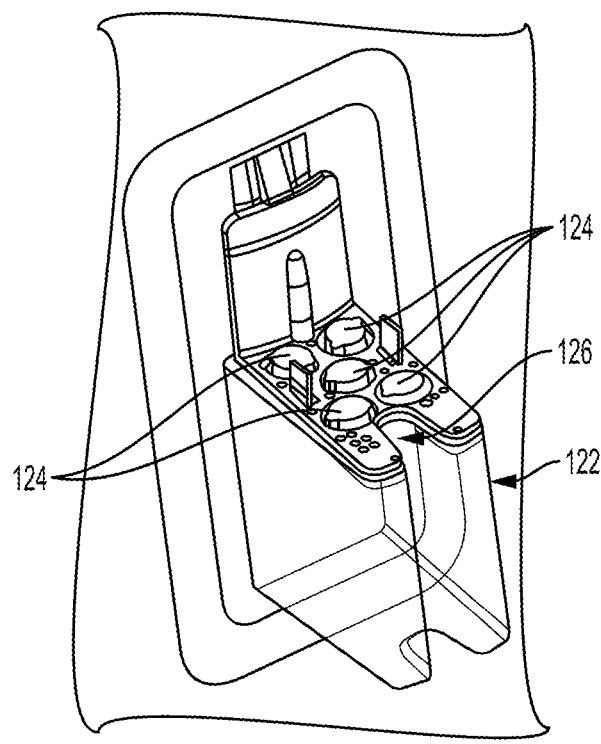
FIG. 5 is a perspective view of a tool driver of the robotic arm of FIG. 4.

FIG. 5 illustrates the tool driver 122 in more detail. As shown, the tool driver 122 includes one or more motors, e.g., five motors 124 are shown, that control a variety of movements and actions associated with the tool 10 coupled to the arm 118. For example, each motor 124 can couple to and/or interact with an activation feature (e.g., gear) associated with the tool 10 for controlling one or more actions and movements that can be performed by the tool 10, such as for assisting with performing a surgical operation. The motors 124 are accessible on the upper surface of the tool driver 122, and thus the tool 10 (e.g., the housing 18 thereof) is configured to mount on top of the tool driver 122 to couple thereto. Exemplary embodiments of motor operation and components of a tool housing (also referred to as a "puck") configured to controlled by tool driver motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

The tool driver 122 also includes a shaft-receiving channel 126 formed in a sidewall thereof for receiving the shaft 12 of the tool 10. In other embodiments, the shaft 12 can extend through on opening in the tool driver 122, or the two components can mate in various other configurations.

Figure 6:
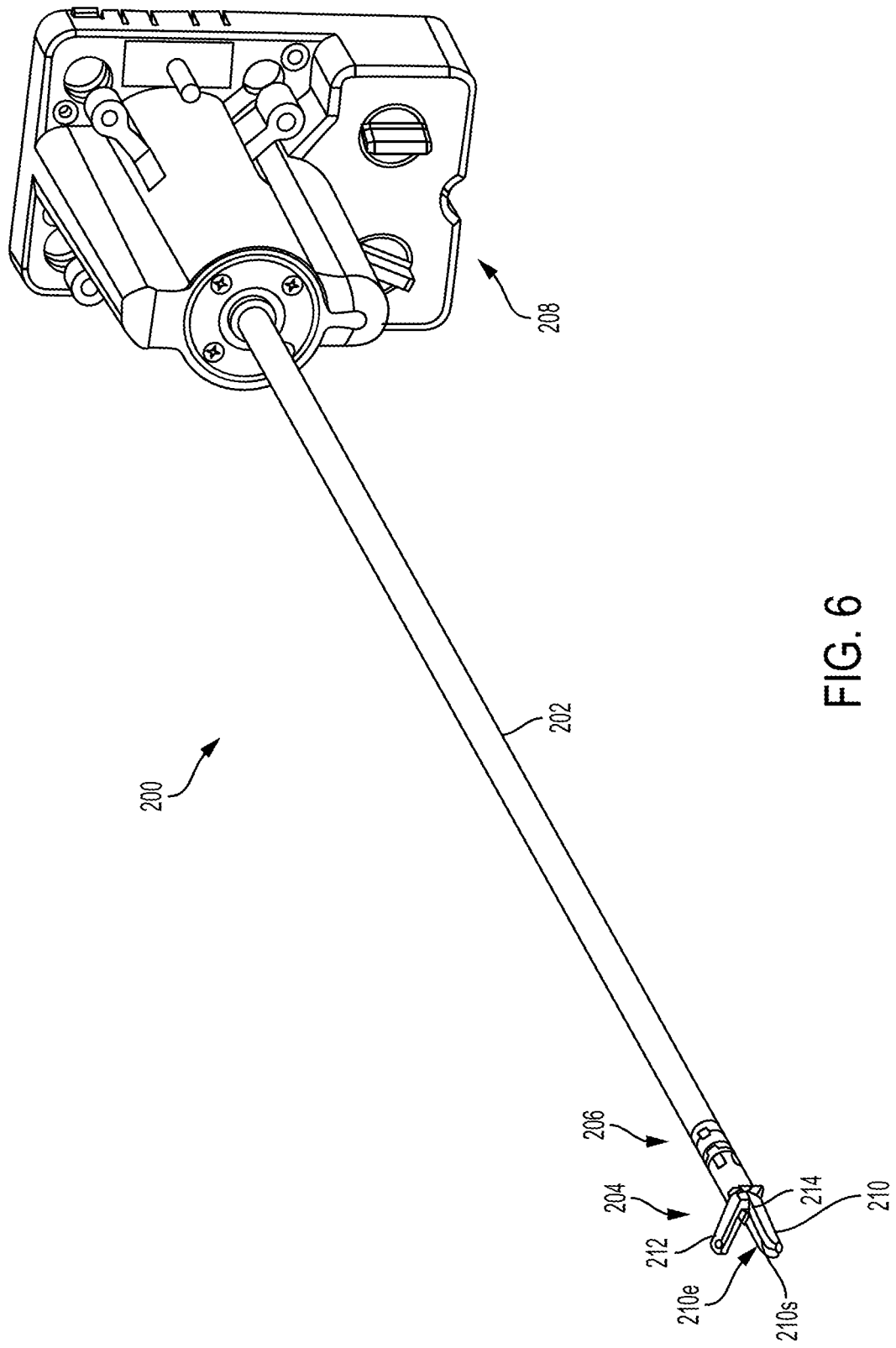
FIG. 6 is a perspective view of another embodiment of a surgical tool.
Figure 7:
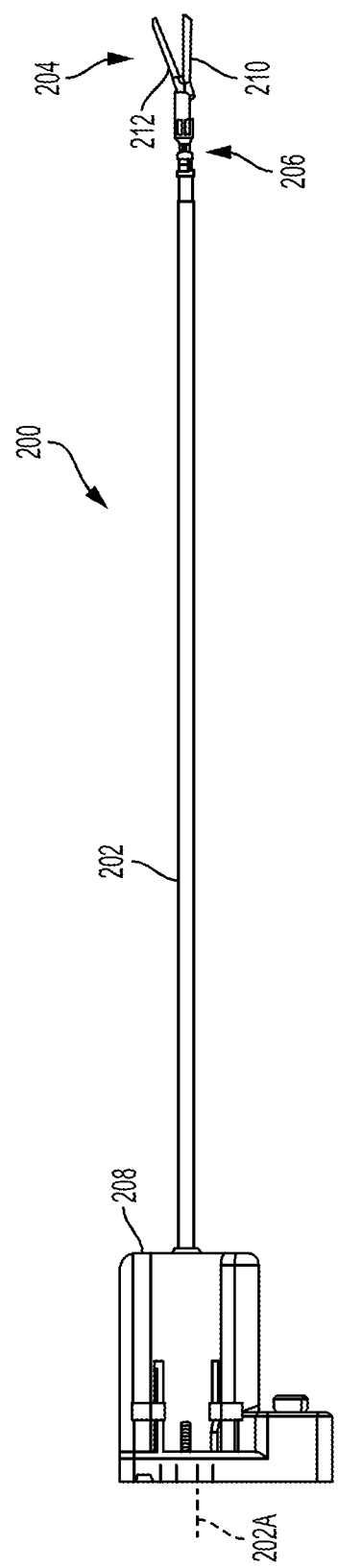
FIG. 7 is a side view of the surgical tool of FIG. 6.
Figure 8:
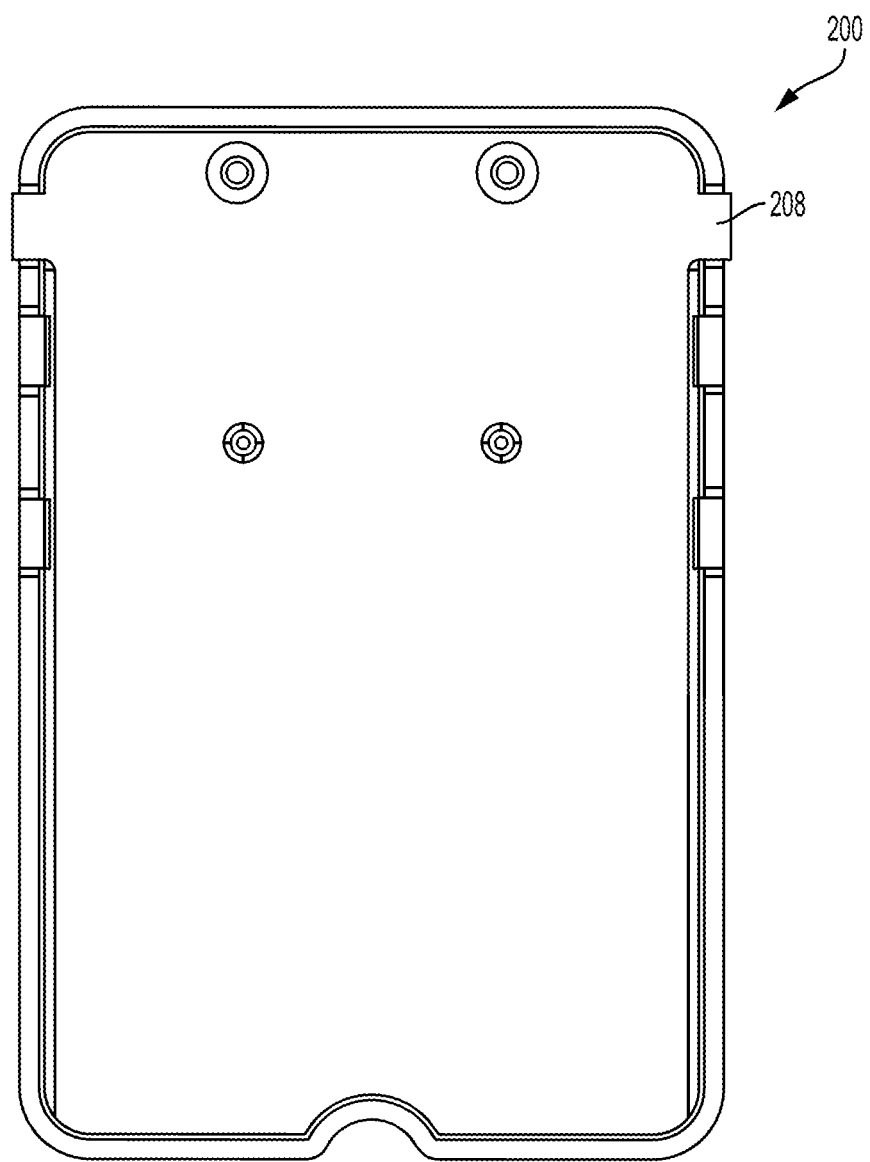
FIG. 8 is a proximal end view of the surgical tool of FIG. 6.
Figure 9:
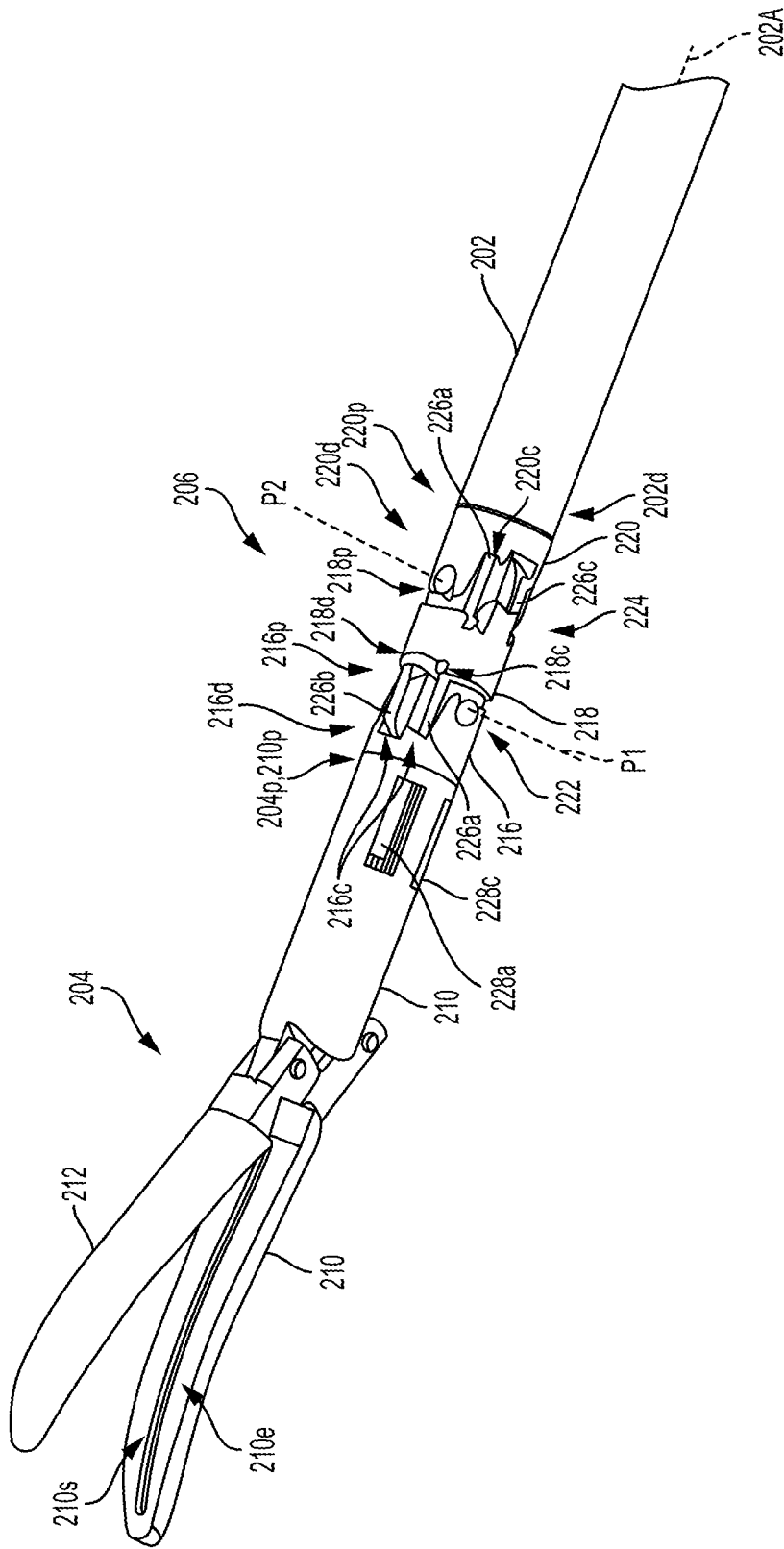
FIG. 9 is a perspective view of a distal portion of the surgical tool of FIG. 6.
Figure 10:
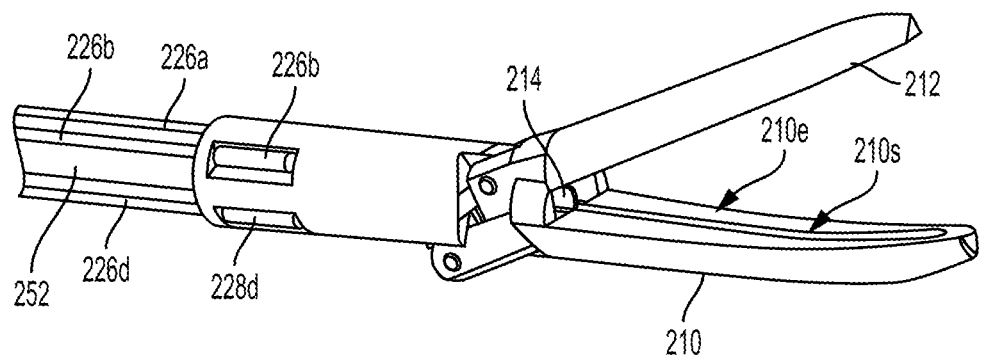
FIG. 10 is another perspective view of a distal portion of the surgical tool of FIG. 6.

FIGS. 6-8 illustrate one embodiment of a surgical tool 200 configured to apply energy to tissue, e.g., is an electrosurgical tool. The tool 200 is generally configured and used similar to the tool 10 of FIG. 1, e.g., includes an elongate shaft 202, an end effector 204, a wrist 206 that couples the end effector 204 to the shaft 202 at a distal end of the shaft 202, and a tool housing 208 coupled to a proximal end of the shaft 202. The tool housing 208 can include a plurality of input interfaces configured to operatively couple a tool driver of a surgical robot to the surgical tool 200. The end effector 204 in this illustrated embodiment includes opposed lower and upper jaws 210, 212. As shown in FIGS. 6 and 9, each of the lower and upper jaws 210, 212 includes an electrode 210e (the upper jaw's electrode is obscured in the figures) configured to deliver energy to tissue engaged between the jaws 210, 212, such as by each of the electrodes 210e receiving one pole from a bipolar energy source to create bipolar energy between the electrodes sufficient to fuse tissue. As shown in FIGS. 6, 9, and 10, each of the lower and upper jaws 210, 212 also includes a slot or groove 210s (the upper jaw's slot or groove is obscured in the figures) extending longitudinally therealong that is configured to slidably receive a cutting element 214 therein to allow the cutting element 214 to cut tissue engaged between the jaws 210, 212. Exemplary embodiments of electrosurgical surgical tools configured to apply energy to tissue including are further described in previously mentioned U.S. Pat. No. 9,055,961 entitled "Fusing And Cutting Surgical Instrument And Related Methods" filed on Feb. 17, 2012.

Figure 11:
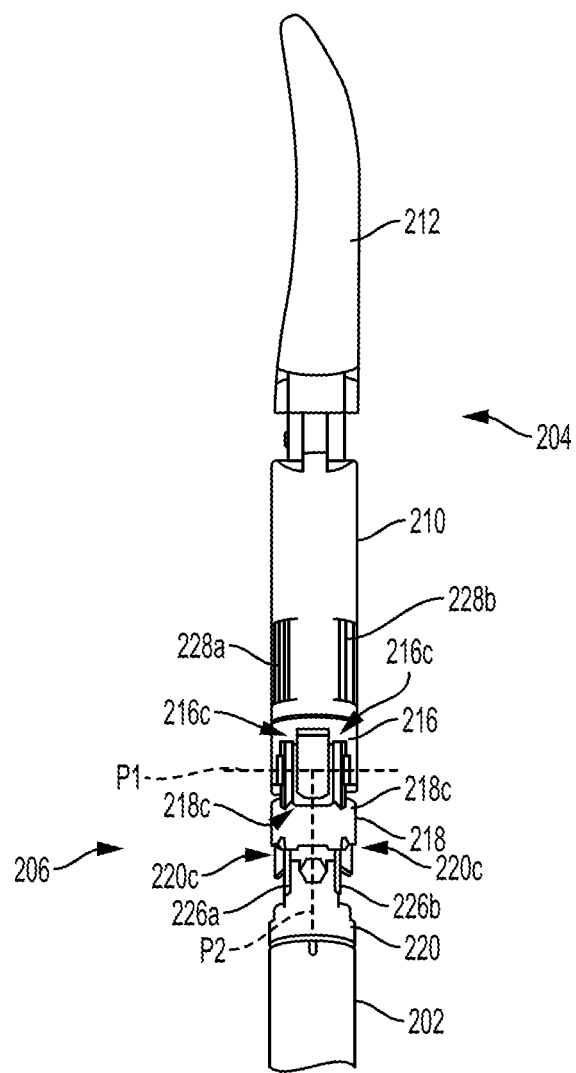
FIG. 11 is a top view of a distal portion of the surgical tool of FIG. 6.

In general, the wrist 206 can allow for fine movements and angulation of the end effector 204 relative to the elongate shaft 202 to which the end effector 204 is coupled. As shown in FIGS. 9 and 11, the tool 200 includes first, second, and third linkages 216, 218, 220 at the wrist 206 that couples the end effector 204 and shaft 202 together. The linkages 216, 218, 220 are configured to facilitate articulation of the end effector 204 relative to the elongate shaft 202, e.g., angle the end effector 204 relative to a longitudinal axis 202A of the elongate shaft 202. A distal end 216d of the first linkage 216 is non-pivotally coupled to a proximal end 204p of the end effector 204, e.g., to a proximal end 210p of the bottom jaw 210. A proximal end 216p of the first linkage 216 is pivotally coupled at a first or distal joint 222 to a distal end 218d of the second linkage 218. A proximal end 218p of the second linkage 218 is pivotally coupled at a second or proximal joint 224 to a distal end of the third linkage 220. A proximal end 220p of the third linkage 220 is non-pivotally coupled a distal end 202d of the elongate shaft 202.

Figure 12:
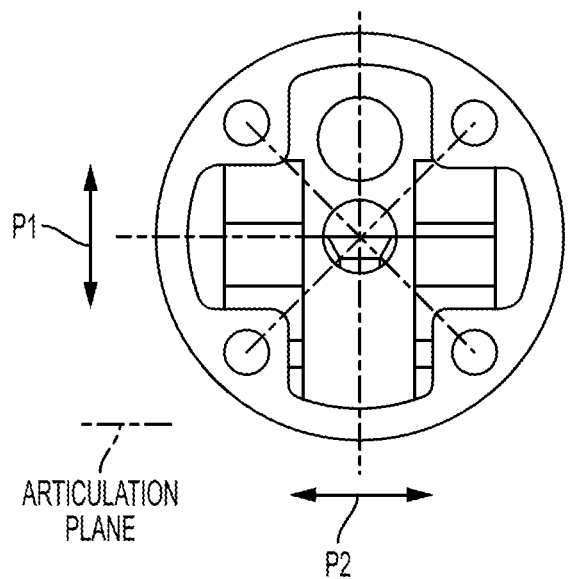
FIG. 12 is a cross-sectional view of the surgical tool of FIG. 6.
Figure 13:
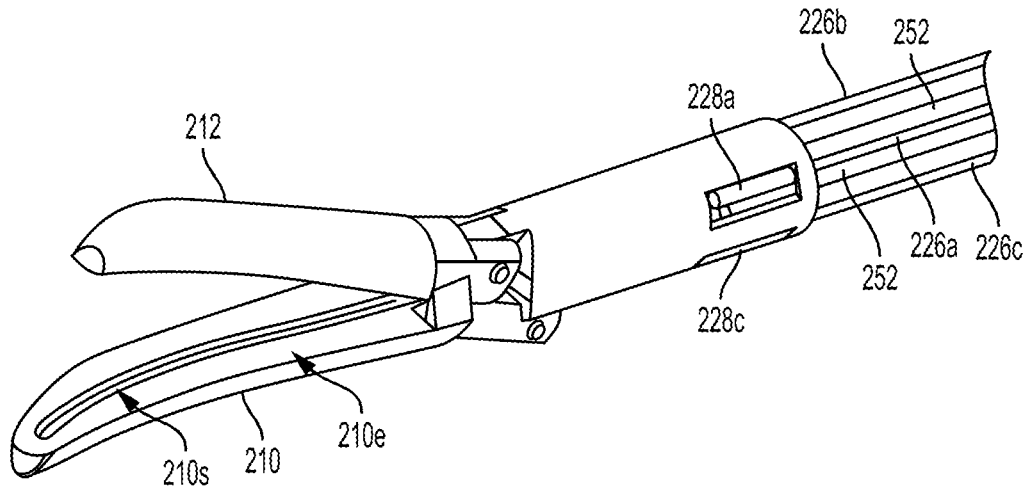
FIG. 13 is another perspective view of a distal portion of the surgical tool of FIG. 6.

As illustrated in FIG. 12, the first joint 222 defines a first pivot axis P1 about which the first linkage 216, and hence the end effector 204 non-pivotally coupled thereto, is configured to pivot relative to the second linkage 218 in pitch motion. The first joint 222 thus defines a first plane in which the first linkage 216, and hence the end effector 204, is configured to move relative to the shaft 202 to adjust the end effector's pitch relative to the shaft 202. The second joint 224 defines a second pivot axis P2 about which the second linkage 218 is configured to pivot relative to the third linkage 220, and hence to the shaft 202 non-pivotally coupled to the third linkage 220, in yaw motion. The second joint 224 thus defines a second plane in which the second linkage 218 is configured to move relative to the third linkage 220, and hence the shaft 202, to adjust the end effector's yaw relative to the shaft 202. The end effector 204 is shown in an unarticulated position in FIGS. 6, 7, 9-11, and 13.

As shown in FIGS. 9-11, 13, and 14, the tool 200 includes first, second, third, and fourth articulation cables 226a, 226b, 226c, 226d configured to be actuated to cause articulating movement of the end effector 204 coupled thereto. The articulation cables 226a, 226b, 226c, 226d are operatively coupled to the tool housing 208 and are thus configured to be operatively coupled to a tool driver, via the tool housing 208. Input from the tool driver to the tool housing 208 can thus be configured to actuate the articulation cables 226a, 226b, 226c, 226d to cause selective movement of selected one or more of the articulation cables 226a, 226b, 226c, 226d to cause selected articulation of the end effector 204.

Figure 14:
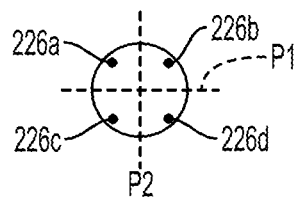
FIG. 14 is a schematic cross-sectional view of the surgical tool of FIG. 6.

In this illustrated embodiment, as shown in FIG. 14, the articulation cables 226a, 226b, 226c, 226d are each offset from the first and second pivot axes P1, P2 and hence are each offset from the first and second planes respectively defined by the first and second pivot axes P1, P2. In other words, the articulation cables 226a, 226b, 226c, 226d are not on either axis P1, P2 of articulation motion. The articulation cables 226a, 226b, 226c, 226d are also spaced radially around the longitudinal axis 202A of the elongate shaft 202 equidistantly from one another at about 45° from the axes P1, P2. This positioning of the articulation cables 226a, 226b, 226c, 226d may allow for the end effector 204 to articulate at a maximum articulation angle in each of pitch and yaw directions of about 80°, e.g., +/−80° for each axis P1, P2.

As shown in FIGS. 9-11 and 13, the articulation cables 226a, 226b, 226c, 226d each extend longitudinally through the first, second, and third linkages 216, 218, 220. Distal ends 228a, 228b, 228c, 229d of each of the articulation cables 226a, 226b, 226c, 226d are fixedly coupled to the end effector 204, e.g., to the bottom jaw 210. The articulation cables' distal ends 228a, 228b, 228c, 229d can be enlarged (e.g., have an enlarged diameter), as in this illustrated embodiment, to facilitate fixed attachment thereof to the end effector 204 via an attachment mechanism such as welding, adhesive, press fit, crimping, etc.

As shown in FIGS. 9 and 11, the first linkage 216 has four channels 216c at its proximal end configured to guide the articulation cables 226a, 226b, 226c, 226d at the first joint 222 during articulation. The second linkage 218 has four channels 218c at its distal end configured to guide the articulation cables 226a, 226b, 226c, 226d at the first joint 222. The second linkage's distal channels 218c and the first linkage's proximal channels 216c can cooperate to guide the 226a, 226b, 226c, 226d around the bend at the first joint 222, thereby helping to prevent the articulation cables 226a, 226b, 226c, 226d from encountering any sharp corners or radii, reducing friction between the articulation cables 226a, 226b, 226c, 226d and the linkage 218 and first linkage 216, and/or helping to prevent the articulation cables 226a, 226b, 226c, 226d from twisting or moving radially inward or outward at the first joint 222 during articulation. Such friction, sharp corners or radii encounters, and twisting or radial movement may exert more force on the articulation cables 226a, 226b, 226c, 226d, which may increase wear on the articulation cables 226a, 226b, 226c, 226d and thereby reduce their overall life. Similarly, the second linkage 218 also has four channels 218c at its proximal end 218p at the second joint 224, and the third linkage 220 has four channels 220c at its distal end 220d at the second joint 224. The second linkage's proximal channels 218c and the third linkage's distal channels 220c can cooperate to guide the 226a, 226b, 226c, 226d around the bend at the second joint 224.

Figure 15:
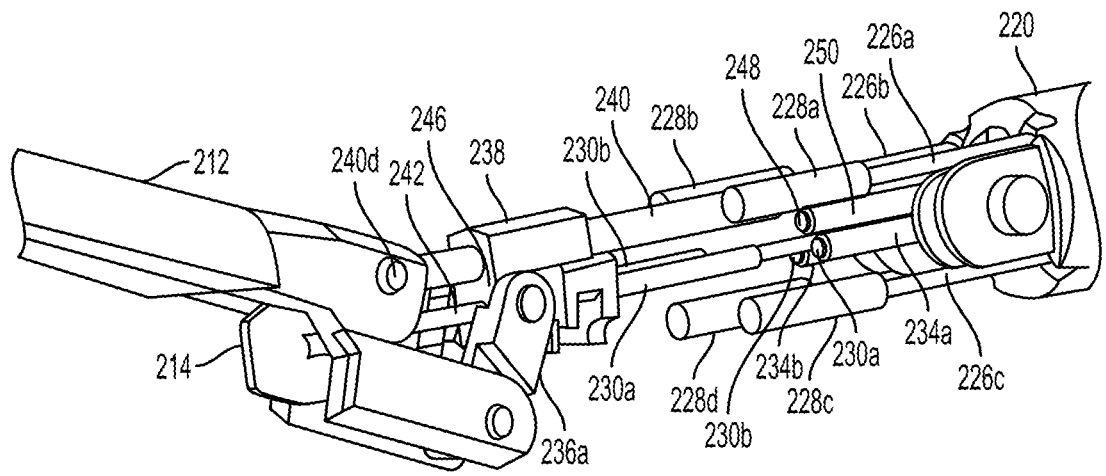
FIG. 15 is a perspective view of the surgical tool of FIG. 6 including a wrist portion thereof.

The end effector 204 is configured to move between an open position in which the jaws 210, 212 are open and a closed position in which the jaws 210, 212 are closed. The end effector 204 is shown in the open position in FIGS. 6, 7, 9-11, and 13. As shown in FIG. 15, the tool 200 includes first and second closure cables 230a, 230b configured to be actuated to cause selective opening and closing of the end effector 204. The closure cables 230a, 230b are operatively coupled to the tool housing 208 and are thus configured to be operatively coupled to a tool driver, via the tool housing 208. Input from the tool driver to the tool housing 208 can thus be configured to actuate the closure cables 230a, 230b to cause selective movement of the closure cables 230a, 230b to cause selected opening and closing of the end effector 204.

Figure 16:
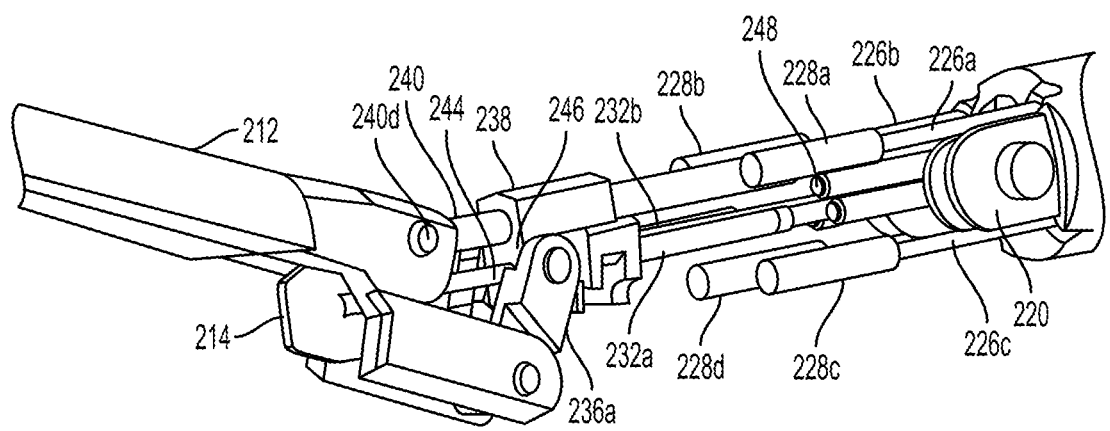
FIG. 16 is another perspective view of the surgical tool of FIG. 6 including a wrist portion thereof.

The closure cables 230a, 230b can have respective distal hypotubes 232a, 232b therearound, as shown in FIG. 16, to help protect the closure cables 230a, 230b and/or to facilitate operative connection of the closure cables 230a, 230b to the end effector 204, e.g., to the upper jaw 212. The closure cables 230a, 230b can also have respective proximal hypotubes 234a, 234b therearound, as shown in FIG. 15, to help protect the closure cables 230a, 230b and/or to facilitate connection of the closure cables 230a, 230b to the tool housing 208.

As shown in FIGS. 9, 10, 13, 15, and 16, the tool 200 includes a pair of links 236a, 236b configured to facilitate the opening and closing of the end effector 204. The links 236a, 236b are on opposed sides, e.g., left and right sides, of the end effector 204. The links 236a, 236b each have distal ends pivotally attached to a hub 238 that is slidably attached to a jaw support rod 240, and each have proximal ends pivotally attached to the top jaw 212. A distal end of the jaw support rod 240 is pivotally attached to the upper jaw 212 with a pivot pin 240d. In response to the actuation of the first and second closure cables 230a, 230b, the first and second closure cables 230a, 230b translate longitudinally, thereby causing the hub 238 to slide either proximally (in response to the closure cables 230a, 230b being pulled proximally) or distally (in response to the closure cables 230a, 230b being pushed distally). Distal movement of the hub 238 (e.g., pushing the closure cables 230a, 230b in a distal direction) pivots the links 236a, 236b downwardly, as shown in FIGS. 15 and 16, to cause the end effector 204 to open. Proximal movement of the hub 238 (e.g., pulling the closure cables 230a, 230b in a proximal direction) pivots the links 236a, 236b upwardly to cause the end effector 204 to close.

As mentioned above, and as shown in FIGS. 15 and 16, the tool 200 includes a cutting element 214 configured to translate along the end effector 204. The cutting element 214 is shown in an initial, proximal position in FIGS. 15 and 16. As shown in FIG. 15, the tool 200 includes a cutting element or blade cable 242 configured to be actuated to cause translation of the cutting element 214 along the end effector 204. The cutting element cable 242 is operatively coupled to the tool housing 208 and are thus configured to be operatively coupled to a tool driver, via the tool housing 208. Input from the tool driver to the tool housing 208 can thus be configured to actuate the cutting element cable 242 to cause movement of the cutting element cable 242 to cause the translation of the cutting element 214 and hence cause the cutting of tissue engaged between the jaws 210, 212. The cutting element cable 242 can have a distal hypotube 244 therearound, as shown in FIG. 16, to help protect the cutting element cable 242 and/or to facilitate longitudinal movement of the cutting element cable 242 through a bore 246 in the hub 238.

As shown in FIGS. 15 and 16, the tool 200 includes an energy or electrical cable 248 configured to provide energy to the electrodes at the end effector 204. The energy cable 248 is operatively coupled to the tool housing 208 and are thus configured to be operatively coupled to a tool driver, via the tool housing 208. Input from the tool driver to the tool housing 208 can thus be configured to actuate the energy cable 248 to selectively cause energy to be delivered to electrodes. The energy cable 248 can have a distal hypotube 250 therearound, as shown in FIG. 15, to help protect the energy cable 248.

Figure 17:
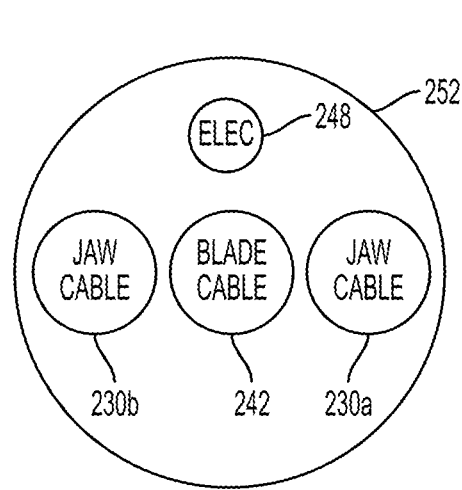
FIG. 17 is a schematic cross-sectional view of the surgical tool of FIG. 6.

As shown in FIGS. 10, 11, and 17, the closure cables 230a, 230b, the cutting element cable 242, and the energy cable 248 can be disposed in and extend through a tube 252. The tube 252 may help protect the closure cables 230a, 230b, the cutting element cable 242, and the energy cable 248. As shown in FIG. 17, the cutting element cable 242 can be substantially coaxial with the longitudinal axis 202A of the shaft 202, which may allow the cutting element cable 242 to align linearly with the slots in the end effector 204 through which the cutting element 214 translates and thereby help prevent bucking of the cutting element cable 242 and/or provide straight cutting. As also shown in FIG. 17, the closure cables 230a, 230b can each extend substantially parallel to the shaft's longitudinal axis 202A, which may help prevent buckling of the closure cables 230a, 230b during longitudinal movement thereof and/or may help the closure cables 230a, 230b be properly aligned with the opposed sides of the end effector 204 with which they are respectively operatively coupled. The energy cable 248 is above the cutting element cable 242 in this illustrated embodiment but can be at any location.

Figure 18:
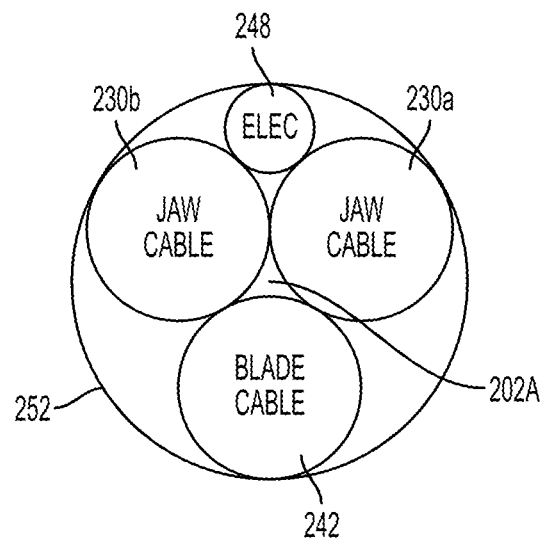
FIG. 18 is a cross-sectional view of the surgical tool of FIG. 6 with a heat shrinked tube.

Initially, as shown in FIG. 18, the tube 252 can be heat shrinked around the closure cables 230a, 230b, the cutting element cable 242, and the energy cable 248. The heat shrinking of the tube 252 can cause the closure cables 230a, 230b, the cutting element cable 242, and the energy cable 248 to abut one another, as shown in FIG. 18. In the heat shrinked tube 252, the closure cables 230a, 230b, the cutting element cable 242, and the energy cable 248 are each offset from the longitudinal axis 202A of the shaft 202 and are arranged therearound. The tube heat shrinked 252 can be fit to the tool 200, and the closure cables 230a, 230b can be moved outward from their position in FIG. 18 to their position in FIG. 17 while the cutting element cable 242 slides therebetween from its position in FIG. 18 to its position in FIG. 17. This movement of the cables 230a, 230b, 242, and movement of the energy cable 248 that may also occur during this transition, may be gentle enough that it can occur over about 5 mm with minimal impact on the cables.

The articulation cables 226a, 226b, 226c, 226d, the closure cables 230a, 230b, the cutting element cable 242, and the energy cable 248 are flexible at least along the wrist 206 to allow for their bending at the first and second joints 222, 224 at the wrist 206. The tube 252 is flexible at least along the wrist 206 to allow for its being at the wrist 206, such as by the tube 252 being formed of a flexible material such as an elastomer and being relatively thin, e.g., about 0.2 mm thick.

FIGS. 19-23 illustrate another embodiment of a wrist 300 of a surgical tool that is configured to apply energy to tissue. The surgical tool is configured and used similar to the surgical tool 200, e.g., includes an elongate shaft 302, an end effector 304, the wrist 300 that couples the end effector 304 to the shaft 302 at a distal end of the shaft 302, a tool housing (not shown) coupled to a proximal end of the shaft 302, electrode(s) (not shown) configured to deliver energy to tissue engaged by the end effector 304, four articulation cables 306a, 306b, 306c, 306d, a cutting element cable 308, a closure cable 312, an energy cable (not shown), a link (not shown) to facilitate end effector opening and closing, a linkage 314 that couples the end effector 304 and shaft 302 together, and a cutting element (not shown). For clarity of illustration, only a proximal portion of the end effector 304 and only a distal portion of the shaft 302 are shown in FIGS. 19-23. In this illustrated embodiment, instead of including a pair of closure cables, the surgical tool of FIGS. 19-23 includes one closure cable 312. As also shown in FIG. 24, the four articulation cables 306a, 306b, 306c, 306d are offset from the axes P3, P4 of articulation at the wrist 300, and the cutting element cable 308 and the closure cable 312 are along each of the axes P3, P4. The cutting element cable 308 and the closure cable 312 are substantially coaxial with a longitudinal axis 302A of the elongate shaft 302. The cutting element cable 308 and the closure cable 312 are disposed in and extend through a tube 316 similar to the tube 252 of the tool 200.

In this illustrated embodiment, the tool has one linkage 314 at the wrist 300. A distal end of the linkage 314 is pivotally coupled at a first or distal joint 318 to a proximal end of the end effector 304. A proximal end of the linkage 314 is pivotally coupled at a second or proximal joint 320 to a distal end of the shaft 302. Similar to the second linkage 218 of the tool 200, the linkage 314 has four channels 314c at its proximal end configured to guide the articulation cables 306a, 306b, 306c, 306d at the first joint 318 during articulation and has four channels 314c at its distal end configured to guide the articulation cables 306a, 306b, 306c, 306d at the second joint 320 during articulation. Similar to the first linkage 216 of the tool 200, the end effector 304 has four channels 304c at its proximal end configured to guide the articulation cables 306a, 306b, 306c, 306d at the first joint 320 during articulation. Similar to the third linkage 220 of the tool 200, the shaft 302 has four channels 302c at its distal end configured to guide the articulation cables 306a, 306b, 306c, 306d at the second joint 320 during articulation.

Figure 19:
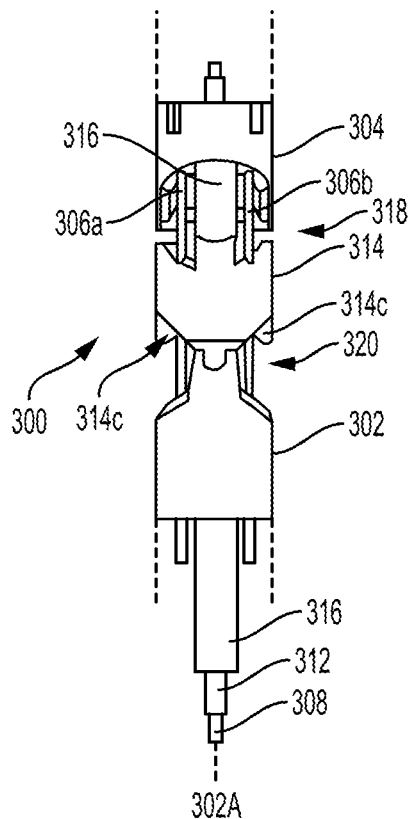
FIG. 19 is a top view of another embodiment of a surgical tool including a wrist portion thereof.
Figure 20:
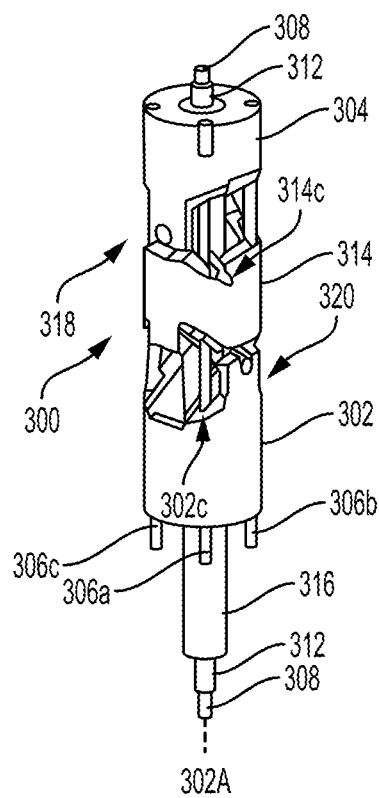
FIG. 20 is a perspective view of the wrist portion of FIG. 19.
Figure 21:
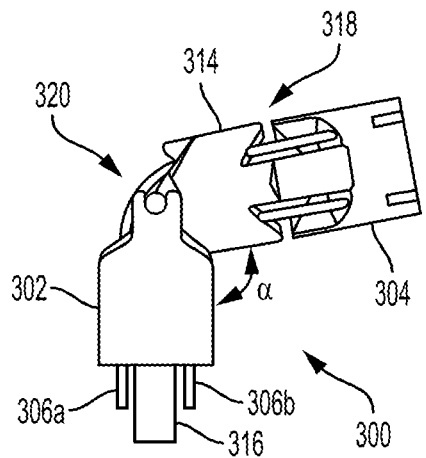
FIG. 21 is a side view of the wrist portion of FIG. 19 articulated in one plane.

FIGS. 19 and 20 show the end effector 304 in an unarticulated position. FIG. 21 shows the end effector 304 articulated from the unarticulated position to an articulated position in which the wrist 300 is bent at the second joint 320, e.g., the end effector 304 and the linkage 314 are angled relative to the shaft 302. The end effector 304 in FIG. 21 has thus adjusted in yaw motion, but not in pitch motion, from its unarticulated position. The end effector 304 is shown in FIG. 21 at a maximum yaw articulation angle α, which is this illustrated embodiment is about 80°. The end effector 304 is shown articulated to the right in this illustrated embodiment, but the end effector 304 can be similarly articulated left up to the maximum yaw articulation angle α. As shown in FIG. 21, the articulation cables 306a, 306b, 306c, 306d are each bent at the second joint 320, e.g., curve around the second joint 320, but remain substantially straight at the first joint 318. All of the articulation cables 306a, 306b, 306c, 306d bend in a same direction at the second joint 320. The articulation cables 306a, 306b, 306c, 306d are guided at the second joint 320 by and are seated in the four channels 314c at the proximal end of the linkage 314 and in the four channels 302c at the distal end of the shaft 302. The cutting element cable 308, closure cable 312, and tube 316 are similarly bent at the second joint 320 but are not bent at the first joint 318, as shown in FIG. 21.

Figure 22:
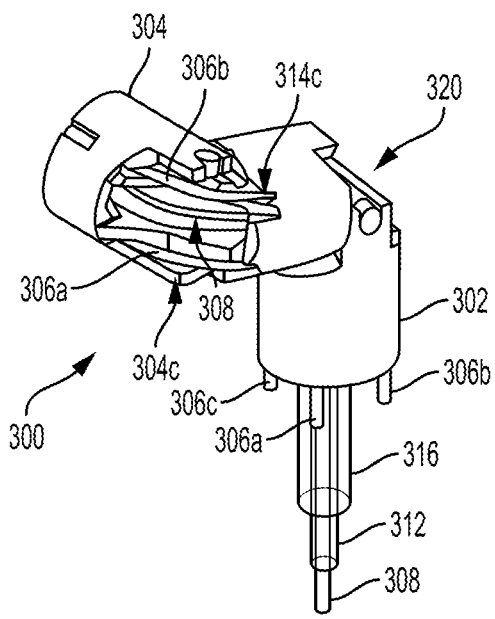
FIG. 22 is a perspective view of the wrist portion of FIG. 19 articulated in two planes.
Figure 23:
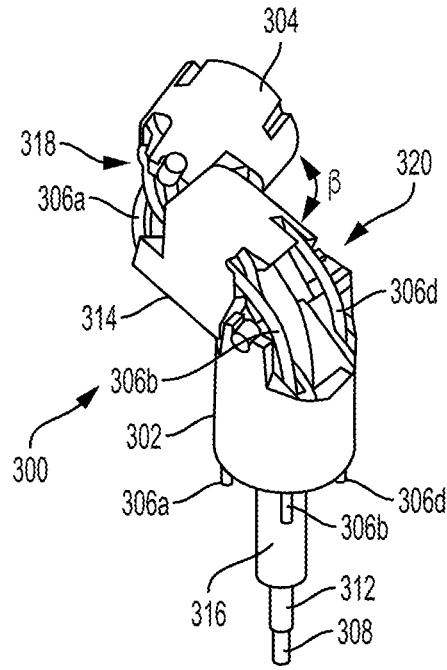
FIG. 23 is another perspective view of the wrist portion of FIG. 22.
Figure 24:
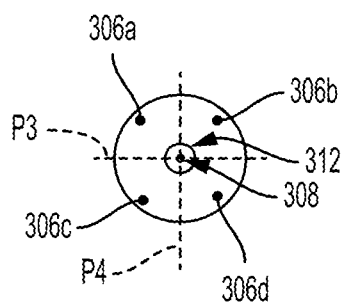
FIG. 24 is a schematic cross-sectional view of the surgical tool of FIG. 19.

FIGS. 22 and 23 show the end effector 304 articulated from the unarticulated position to another in which the wrist 300 is bent at each of the first and second joints 318, 320, e.g., the end effector 304 and the linkage 314 are angled relative to the shaft 302 (at the second joint 320) and the end effector 304 is also angled relative to the linkage 314 (at the first joint 318). The end effector 304 in FIGS. 22 and 23 has thus adjusted in yaw motion and in pitch motion. The end effector 304 is shown in FIGS. 22 and 23 angled to the left at the maximum yaw articulation angle α and angled down at a maximum pitch articulation angle β, which is this illustrated embodiment is about 80°. The end effector 304 can be similarly articulated upward up to the maximum pitch articulation angle β. As shown in FIGS. 22 and 23, the articulation cables 306a, 306b, 306c, 306d are each bent at the second joint 320 and are also bent at the first joint 318. All of the articulation cables 306a, 306b, 306c, 306d bend in a same direction at the first joint 318, which is a direction substantially perpendicular to the direction at the second joint 320, e.g., pitch movement about the first axis P3 and yaw movement about the second axis P4. The articulation cables 306a, 306b, 306c, 306d are guided at the second joint 320 by and are seated in the four channels 314c at the proximal end of the linkage 314 and in the four channels 302c at the distal end of the shaft 302. Also, the articulation cables 306a, 306b, 306c, 306d are guided at the first joint 318 by and are seated in the four channels 314c at the distal end of the linkage 314 and in the four channels 302c at the proximal end of the end effector 304. The cutting element cable 308, closure cable 312, and tube 316 are similarly bent at the first and second joints 318, 320, as shown in FIGS. 22 and 23.

Figure 25:
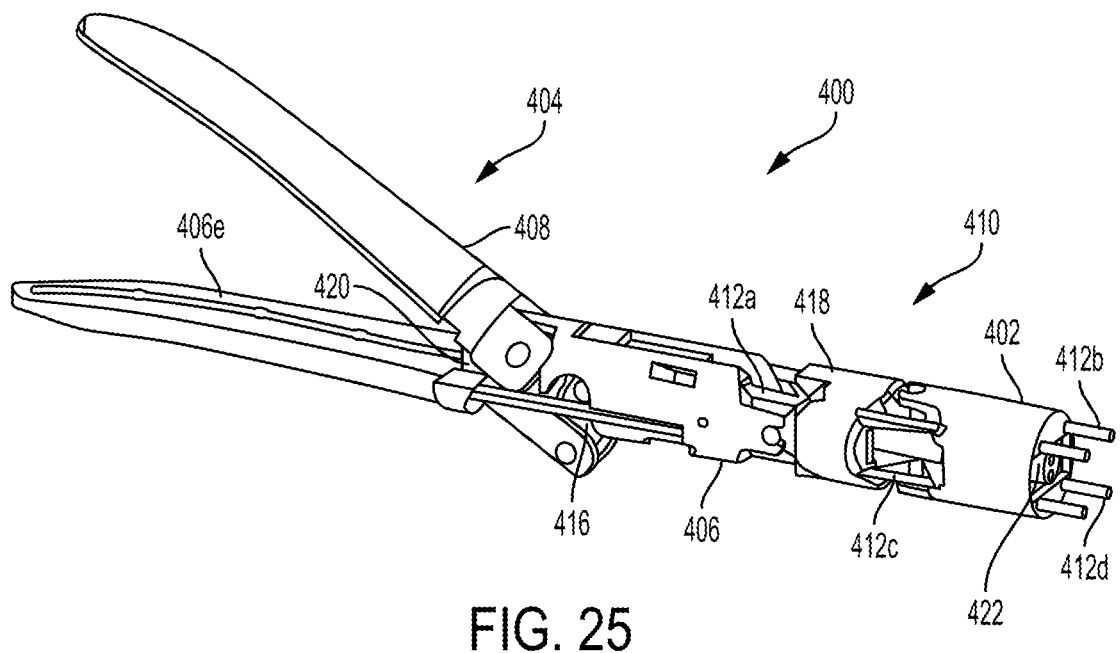
FIG. 25 is a perspective view of a distal portion of another embodiment of a surgical tool with an end effector thereof in an open position.
Figure 25A:
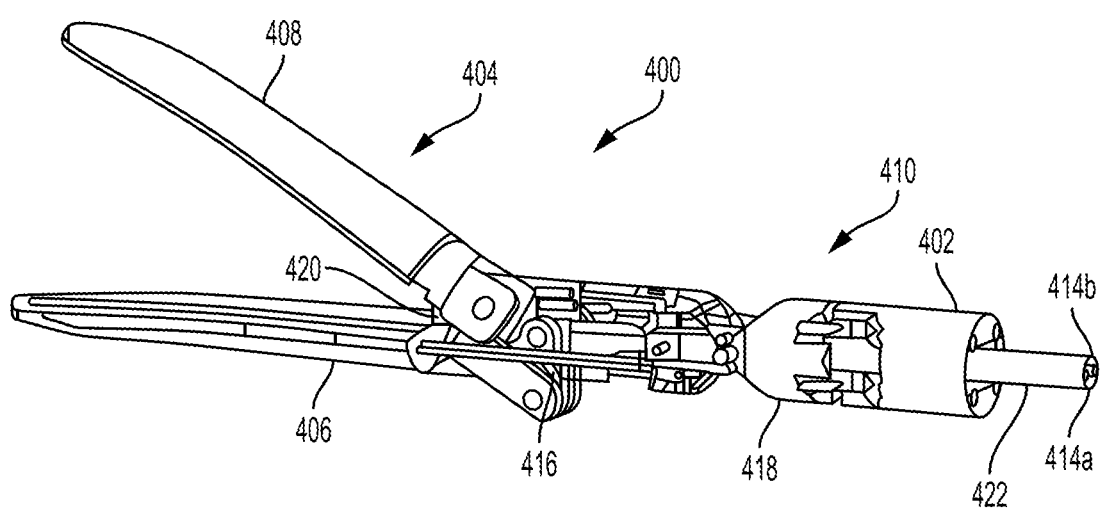
FIG. 25A is a partially transparent view of the distal portion of the surgical tool of FIG. 25.
Figure 26:
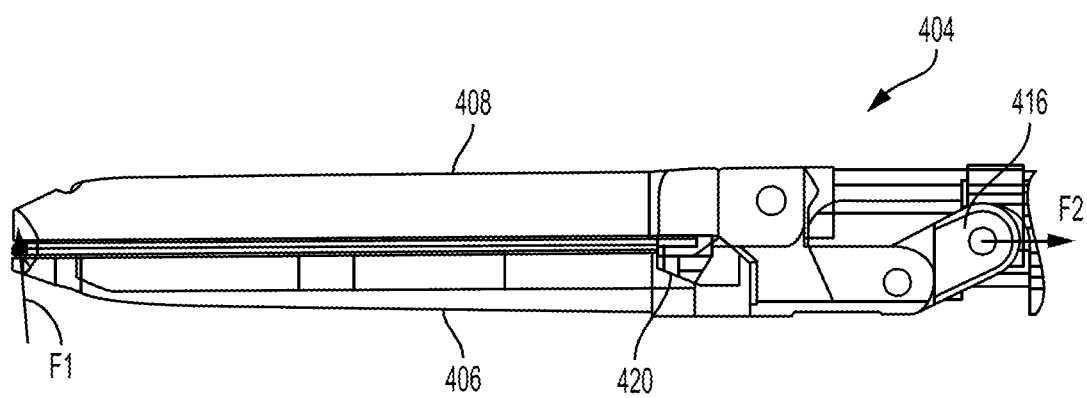
FIG. 26 is a side view of a distal portion of the surgical tool of FIG. 25 with the end effector in a closed position.
Figure 27:
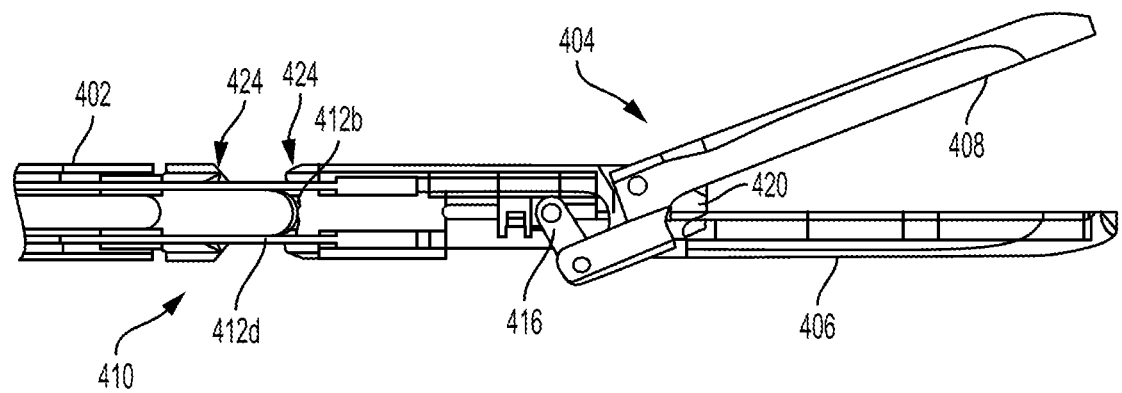
FIG. 27 is a side view of a distal portion of the surgical tool of FIG. 25.

FIGS. 25-27 illustrate another embodiment of a surgical tool 400 configured to apply energy to tissue. The surgical tool 400, only a distal portion of which is shown in FIGS. 25-27, is configured and used similar to the surgical tool 200, e.g., includes an elongate shaft 402, an end effector 404 that includes lower and upper jaws 406, 408, a wrist 410 that couples the end effector 404 to the shaft 402 at a distal end of the shaft 402, a tool housing (not shown) coupled to a proximal end of the shaft 402, an electrode 406e at the lower jaw 406 configured to deliver energy to tissue engaged by the end effector 404, an electrode (not shown) at the upper jaw 408 configured to deliver energy to tissue engaged by the end effector 404, four articulation cables 412a, 412b, 412c, 412d, a cutting element cable (not shown), a pair of closure cables 414a, 414b, an energy cable (not shown), a pair of links 416 to facilitate end effector opening and closing, a linkage 418 that couples the end effector 404 and shaft 402 together, and a cutting element 420. For clarity of illustration, the articulation cables 412a, 412b, 412c, 412d are omitted from FIG. 26, and the closure cables 414a, 414b are omitted from FIGS. 25 and 25A. Similar to the embodiment of FIGS. 19-23, the wrist 410 in the embodiment of FIGS. 25-27 includes a single linkage 418, and the linkage 418, end effector 404, and shaft 402 include channels 424 (only two of which are labeled in FIG. 27) configured to guide the articulation cables 412a, 412b, 412c, 412d. Also similar to the embodiment of FIGS. 19-23, the closure cables 414a, 414b, cutting element cable, and energy cable are disposed in and extend through a central tube 422, except that instead of one closure cable 312 this illustrated embodiment has a pair of closure cables 414a, 414b that are offset from center similar to the closure cables 230a, 230b of the surgical tool 200 of FIG. 15. FIGS. 25, 25A, and 27 illustrate the end effector 404 in an open position, and FIG. 26 illustrates the end effector 404 in a closed position. FIGS. 25-27 illustrate the end effector 404 in an unarticulated position.

FIG. 26 illustrates a clamping force F1 configured to be provided at a distal tip of the end effector 404 when the end effector 404 is in the closed position. The end effector 404 can provide the clamping force F1 to tissue clamped between the jaws 406, 408. For clarity of illustration, tissue is not shown clamped between the jaws 406, 408 in FIG. 26. FIG. 26 also illustrates an actuation force F2 exerted in a proximal direction on the closure cables 414a, 414b to hold the end effector 404 in the closed position. The pair of links 416 allows the actuation force F2 to be less than in other end effectors, such as end effector using a pin of one jaw that slides in a slot of the other jaw to effect jaw movement, while achieving the same clamping force F1. For example, a clamping force F1 for the end effector 404 of about 22 N (about 5 lbs) can be achieved with an actuation force F2 of about 115 N (about 26 lbs).

Figure 28:
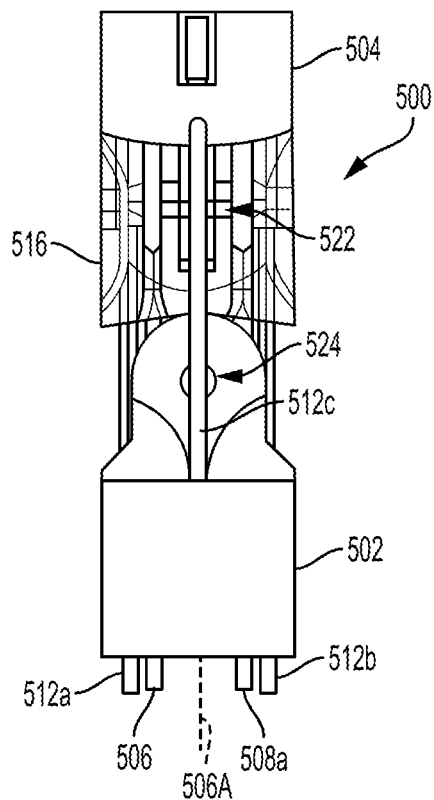
FIG. 28 is a side view of yet another embodiment of a surgical tool including a wrist portion thereof.
Figure 29:
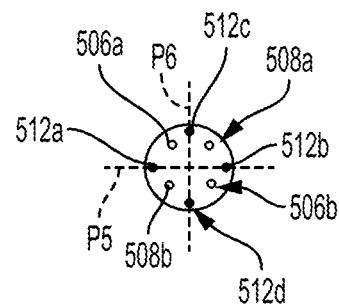
FIG. 29 is a schematic cross-sectional view of the surgical tool of FIG. 28.
Figure 30:
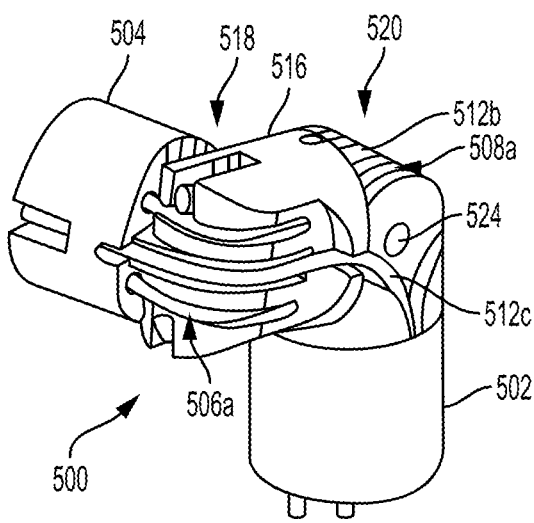
FIG. 30 is a perspective view of the wrist portion of FIG. 28 articulated in two planes.
Figure 31:
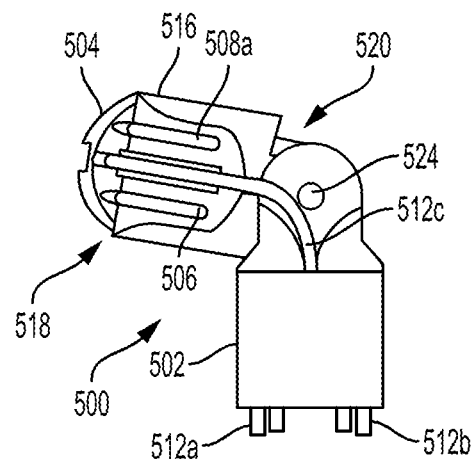
FIG. 31 is another perspective view of the wrist portion of FIG. 30.
Figure 32:
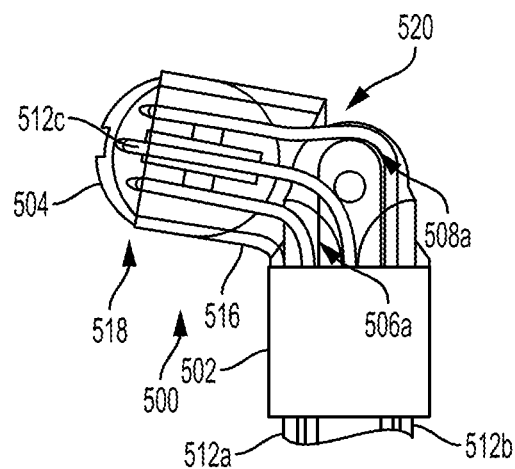
FIG. 32 is a partially transparent view of the wrist portion of FIG. 31.

FIGS. 28-32 illustrate another embodiment of a wrist 500 of a surgical tool that is configured to apply energy to tissue. The surgical tool is configured and used similar to the surgical tool 200, e.g., includes an elongate shaft 502, an end effector 504, the wrist 500 that couples the end effector 504 to the shaft 502 at a distal end of the shaft 502, a tool housing (not shown) coupled to a proximal end of the shaft 502, electrode(s) (not shown) configured to deliver energy to tissue engaged by the end effector 504, four articulation cables 512a, 512b, 512c, 512d, a cutting element cable having trailing ends 506a, 506b, a pair of closure cables 508a, 508b, an energy cable (not shown), a link (not shown) to facilitate end effector opening and closing, a linkage 516 that couples the end effector 504 and shaft 502 together, and a cutting element (not shown). For clarity of illustration, only a proximal portion of the end effector 504 and only a distal portion of the shaft 502 are shown in FIGS. 28-31. FIG. 28 illustrates the end effector 504 in an unarticulated position, and FIGS. 30-32 illustrate the end effector 504 in an articulated position in which the wrist 500 is bent at the tool's first and second joints 518, 520.

In this illustrated embodiment, as shown in FIG. 29, the articulation cables 512a, 512b, 512c, 512d are each on-axis with one or the other of first and second pivot axes P5, P6 defined by the first and second joints 518, 520, respectively. The articulation cables 512a, 512b, 512c, 512d are thus in first and second planes respectively defined by the first and second pivot axes P5, P6. In other words, the articulation cables 512a, 512b, 512c, 512d are on the axes P5, P6 of articulation motion. The articulation cables 512a, 512b, 512c, 512d are also spaced radially around the elongate shaft's longitudinal axis 502A. Also as shown in FIG. 29, the closure cables 508a, 508b and the trailing ends 506a, 506b of the cutting element cable are each offset from the first and second pivot axes P5, P6 and are spaced radially around the elongate shaft's longitudinal axis 502A. The closure cables 508a, 508b are diagonally opposed from one another, and the trailing ends 506a, 506b of the cutting element cable are diagonally opposed from one another.

Two of the articulation cables 512c, 512d that are offset about 180° from each other have distal ends attached to the end effector 504 such that the articulation cables 512c, 512d extend across both of the first and second joints 518, 520, similar to that discussed above regarding the tool 200 of FIGS. 6-8. These two articulation cables 512c, 512d are configured to provide one plane of motion at the second joint 520. The other two articulation cables 512a, 512b that are offset about 180° from each other have distal ends attached to the linkage 516 such that the articulation cables 512a, 512b extend across the first joint 518 and terminate proximal to the second joint 520 so as to not extend across the second joint 520. These two articulation cables 512a, 512b are configured to provide another plane of motion at the first joint 518.

As shown in FIG. 28, a first pivot pin 522 is at the first or distal joint 522 pivotally connecting the end effector 504 and the linkage 516, and a second pivot pin 524 is at the second or proximal joint 524 pivotally connecting the linkage 516 and the shaft 502. The second pivot pin 524 is shorter than the first pivot pin 522, which allows clearance room for the two articulation cables 512c, 512d to pass through the second joint 520 and the linkage 516 so the two articulation cables 512c, 512d can extend to the end effector 504 and have their distal ends attached thereto as discussed above. These two articulation cables 512c, 512d thus extend along the linkage 516 exterior to, or radially outward from, the second pivot pin 524. The closure cables 512a, 512b and the trailing ends 506a, 506b of the cutting element cable are located in the spaces between the first and second pivot pins 522, 524.

The cutting element cable is configured to operatively couple to a pulley at the end effector 504 to effect translational movement of the cutting element along the end effector 504. One of the trailing ends 506a of the cutting element cable extends proximally from one side of the pulley, and the other of the trailing ends 506b extends proximally from the other side of the pulley. Pulling one of the trailing ends 506a, 506b proximally is configured to translate the cutting element distally along the end effector 504, e.g., to cause cutting of tissue engaged by the end effector 504, with the cutting element cable sliding along the pulley. Pulling the other one of the trailing ends 506a, 506b proximally is configured to translate the cutting element proximally along the end effector 504, e.g., to retract the cutting element, with the cutting element cable sliding along the pulley. When the end effector 504 is articulated at one or both of the joints 518, 520, the cutting element cable being pulled proximally to actuate the cutting element more easily bends or flexes the cutting element cable at the pivoted one or both of the joints 518, 520, as compared to the cutting element cable being pushed distally. The cutting element cable may thus not be subjected to buckling loads, thereby reducing chances of cable failure and/or increasing an overall life of the cable.

FIGS. 33-36 illustrates one embodiment of an end effector 600 including a pulley 602 configured to be operatively engaged with a cutting element cable 604 having first and second trailing ends 604a, 604b, such as the cutting element cable of FIGS. 28-32, to cause selective proximal and distal translation of a cutting element 606 along the end effector 600. The end effector 600 is generally configured and used similar to the end effector 204 of the tool 200 of FIGS. 6-8, e.g., includes a pair of opposed jaws 608, 610, includes electrode(s) (obscured in FIGS. 33-36) on each of the jaws 608, 610, and is configured to articulate at a wrist relative to an elongate shaft of the surgical tool that includes the end effector 600. Including the pulley 602 in the end effector 600, e.g., in the lower jaw 608, does not add any dead space in the end effector 600.

Figure 33:
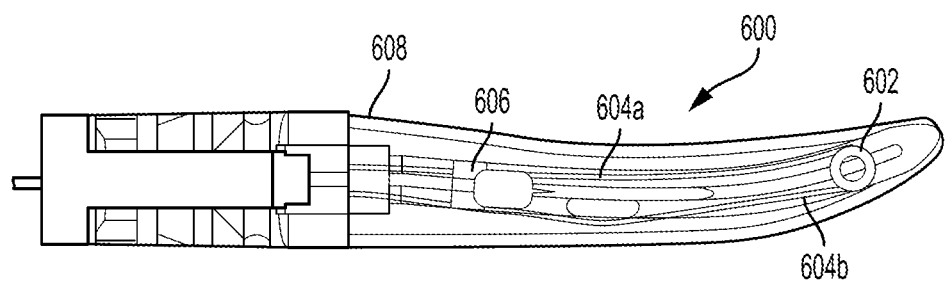
FIG. 33 is a top, partially transparent view of a distal portion of another embodiment of a surgical tool.
Figure 34:
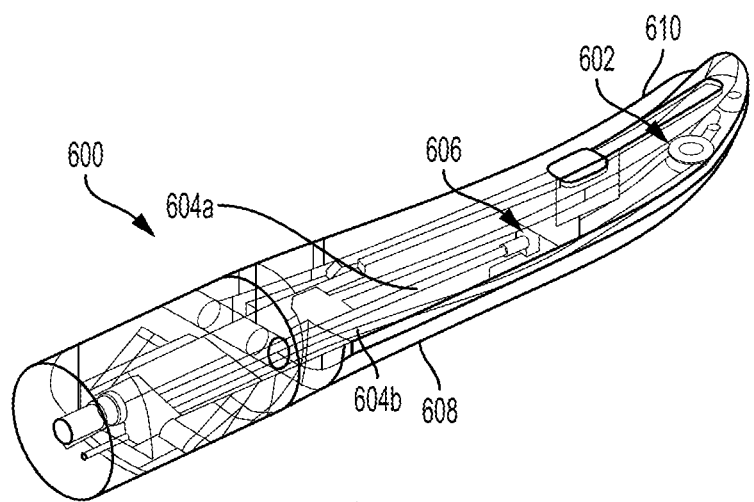
FIG. 34 is a perspective view of the distal portion of the surgical tool of FIG. 33.

The cutting element 606 is attached to a first one of the trailing ends 604a of the cutting element cable 604. Pulling the first trailing end 604a of the cutting element cable 604 causes the cutting element 606 to translate distally along the end effector 600. FIG. 33 shows the cutting element 606 distally advanced from an initial position thereof in response to pulling of the first trailing end 604a of the cutting element cable 604 in a proximal direction, e.g., in response to actuation thereof by a robotic surgical system coupled to the surgical tool. FIG. 34 shows the cutting element 606 distally advanced from its position in FIG. 33. FIGS. 35 and 36 show the cutting element 606 distally advanced from its position in FIG. 34 and at a distal-most position of the cutting element 606 relative to the end effector 600. Further pulling of the first trailing end 604a of the cutting element cable 604 with the cutting element 606 at its distal-most position will not cause movement of the cutting element 606. Instead, pulling the second trailing end 604b of the cutting element cable 604 with the cutting element 606 at its distal-most position will cause the cutting element 606 to move proximally along the end effector 600 back to its initial position.

A surgical tool, such as the surgical tools configured to apply energy to tissue described herein, can include a cable management guide configured to accommodate any slack of the tool's articulation cables during articulation of the tool's end effector. FIG. 37 illustrates one embodiment of a cable management guide 700 of a surgical tool. The cable management guide 700 is shown incorporated into the tool 400 of FIGS. 25-27, with the cable management guide 700 being at a second or proximal joint between the elongate shaft 402 and the linkage 418. The cable management guide 700 includes a pair of opposed, oval-shaped plates. The plates are configured to accommodate any slack of the tool's articulation cables 412a, 412b, 412c, 412d during articulation of the end effector 404. The cable management guide 700 in this illustrated embodiment has an offset of about 1.1 mm when the end effector 404 is articulated, as shown in FIG. 37, which may allow the lengths of the articulation cables 412a, 412b, 412c, 412d to be substantially constant, e.g., with a maximum delta no greater than about 0.07 mm. The cable management guide can have other shapes. For example, FIG. 38 illustrates an embodiment of a cable management guide 702 in the form of a pair of opposed circular plates at the second or proximal joint between the elongate shaft 402 and the linkage 418. FIG. 39 illustrates another embodiment of a cable management guide 704 in the form of a pair of opposed circular plates, which have smaller diameters than the plates of FIG. 38, at the second or proximal joint between the elongate shaft 402 and the linkage 418.

Figure 40:
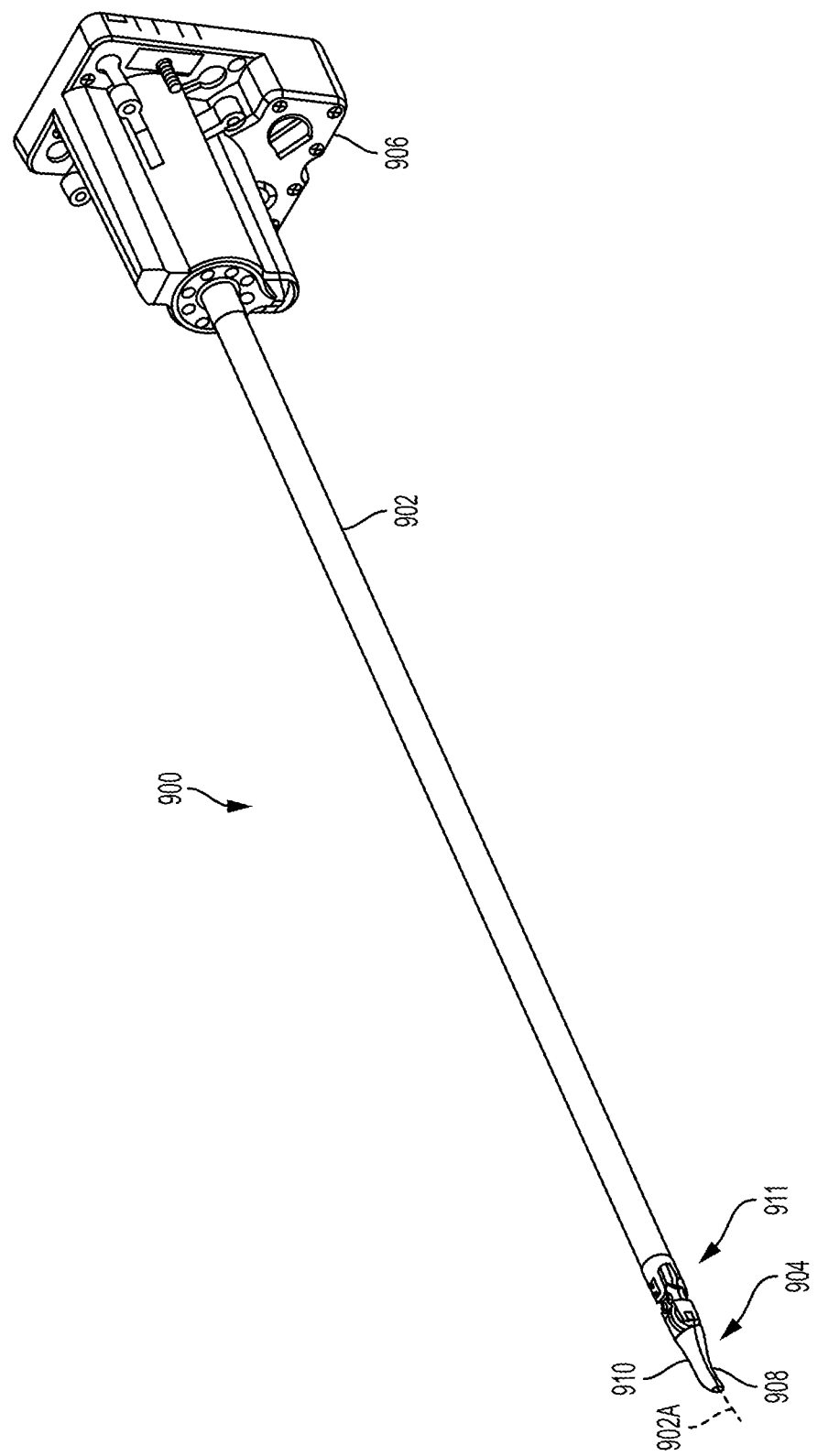
FIG. 40 is a perspective view of another embodiment of a surgical tool.
Figure 41:
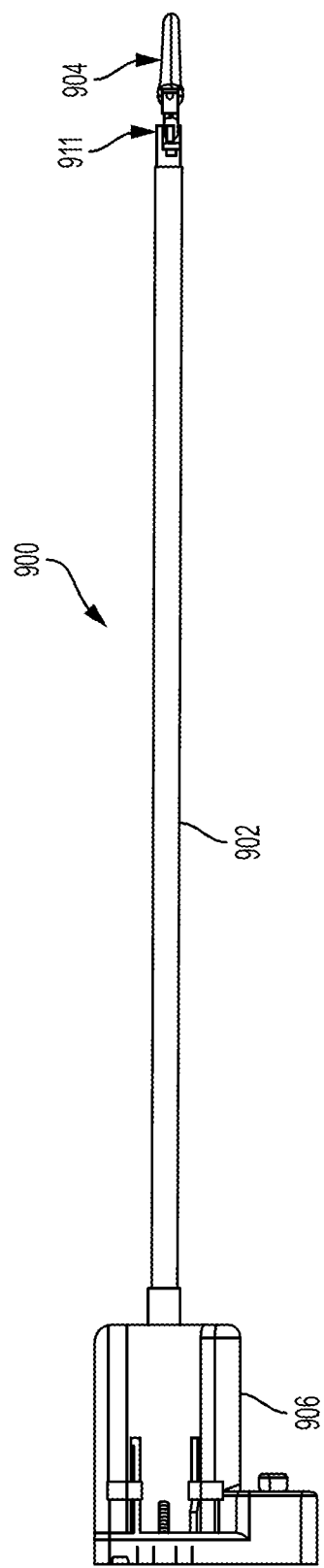
FIG. 41 is a side view of the surgical tool of FIG. 40.
Figure 42:
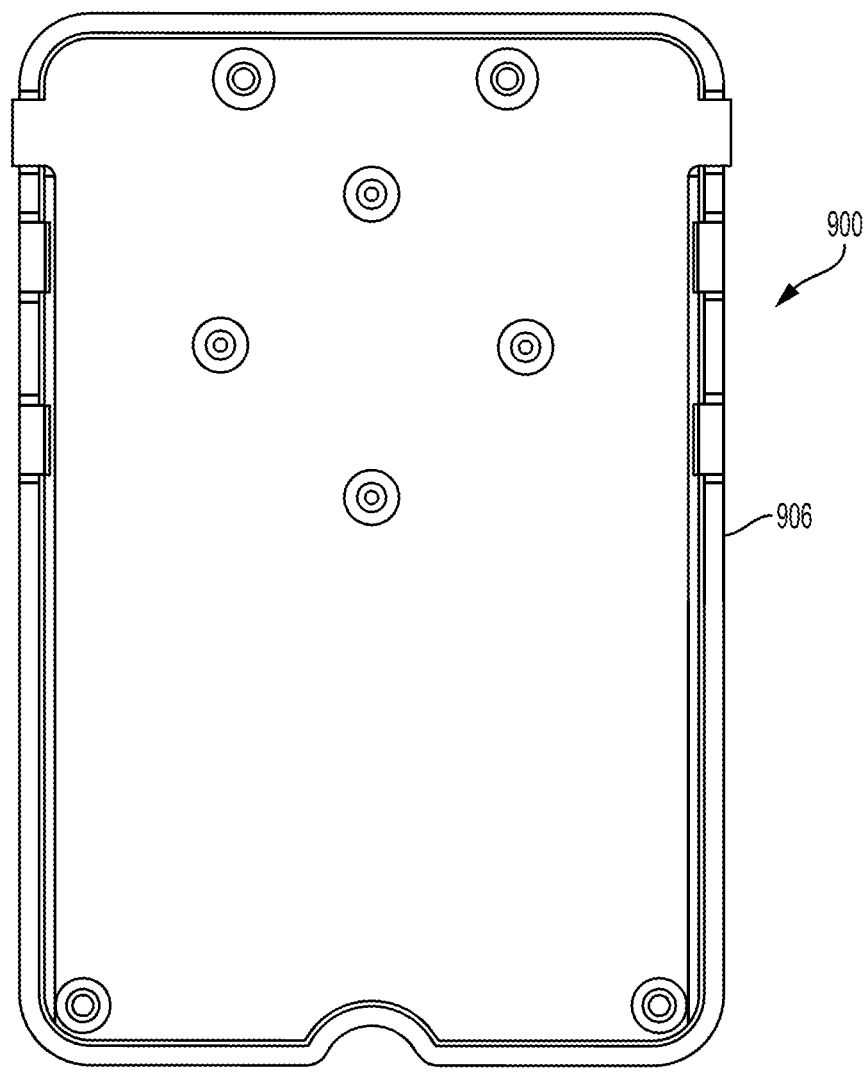
FIG. 42 is a proximal end view of the surgical tool of FIG. 40.

FIGS. 40-42 illustrate another embodiment of a surgical tool 900 configured to apply energy to tissue. The surgical tool 900 is configured and used similar to the surgical tool 200, e.g., includes an elongate shaft 902, an end effector 904 that includes opposed jaws 908, 910, a wrist 911 that couples the end effector 904 to the shaft 902 at a distal end of the shaft 902, a tool housing 906 coupled to a proximal end of the shaft 902, electrode(s) (obscured in FIGS. 40-42) configured to deliver energy to tissue engaged by the end effector 904, a first articulation and closure cable looped around the jaws 908, 910 and having trailing ends 912a, 912c and a second articulation and closure cable looped around the jaws 908, 910 and having trailing ends 912b, 912d (see FIGS. 44 and 45), a pair of cutting element cables 914a, 914b (see FIGS. 44 and 45), an energy cable (not shown), and a cutting element (obscured in FIGS. 40-42). The end effector 904 is illustrated in FIGS. 40, 41, and 43-45 in an unarticulated position and in a closed position. The tool housing 906 in this illustrated embodiment has six input interfaces.

Figure 43:
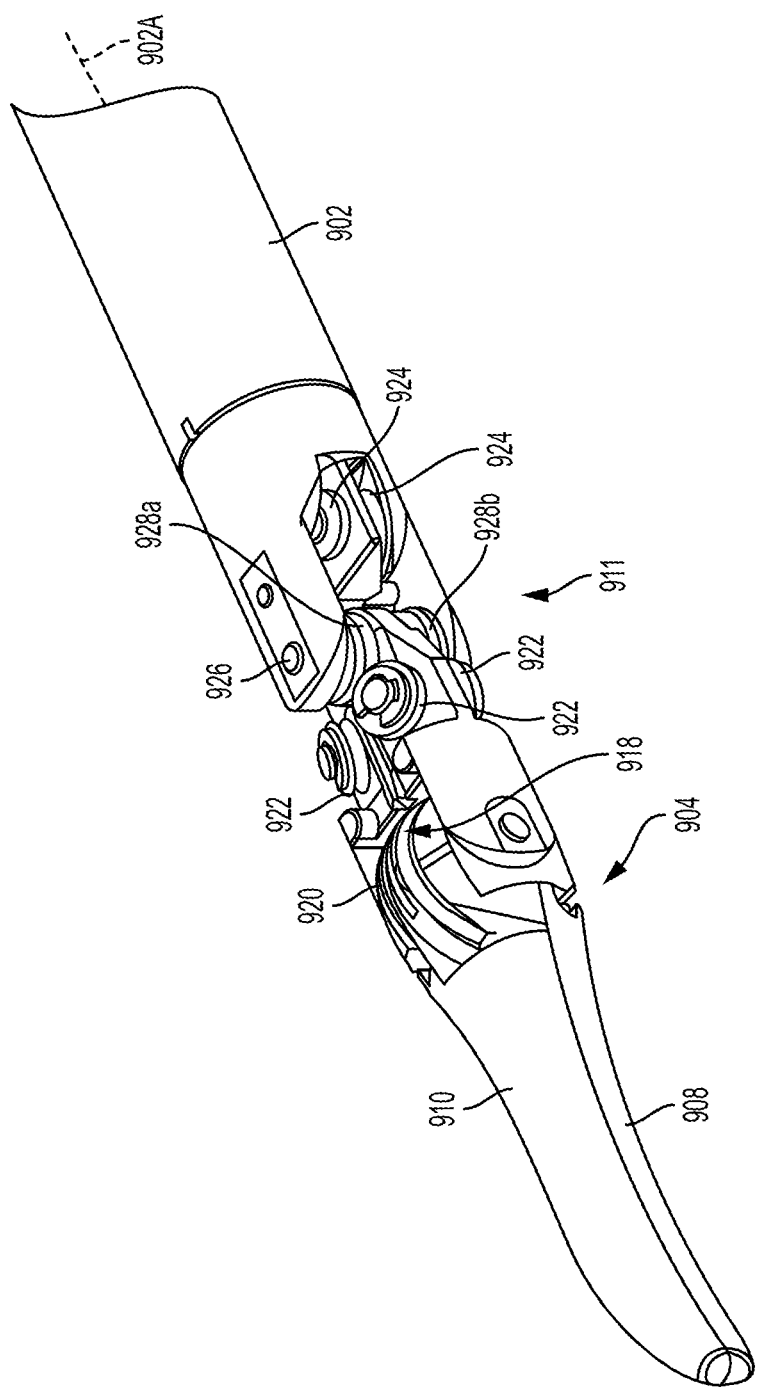
FIG. 43 is a perspective view of a distal portion of the surgical tool of FIG. 40.
Figure 44:
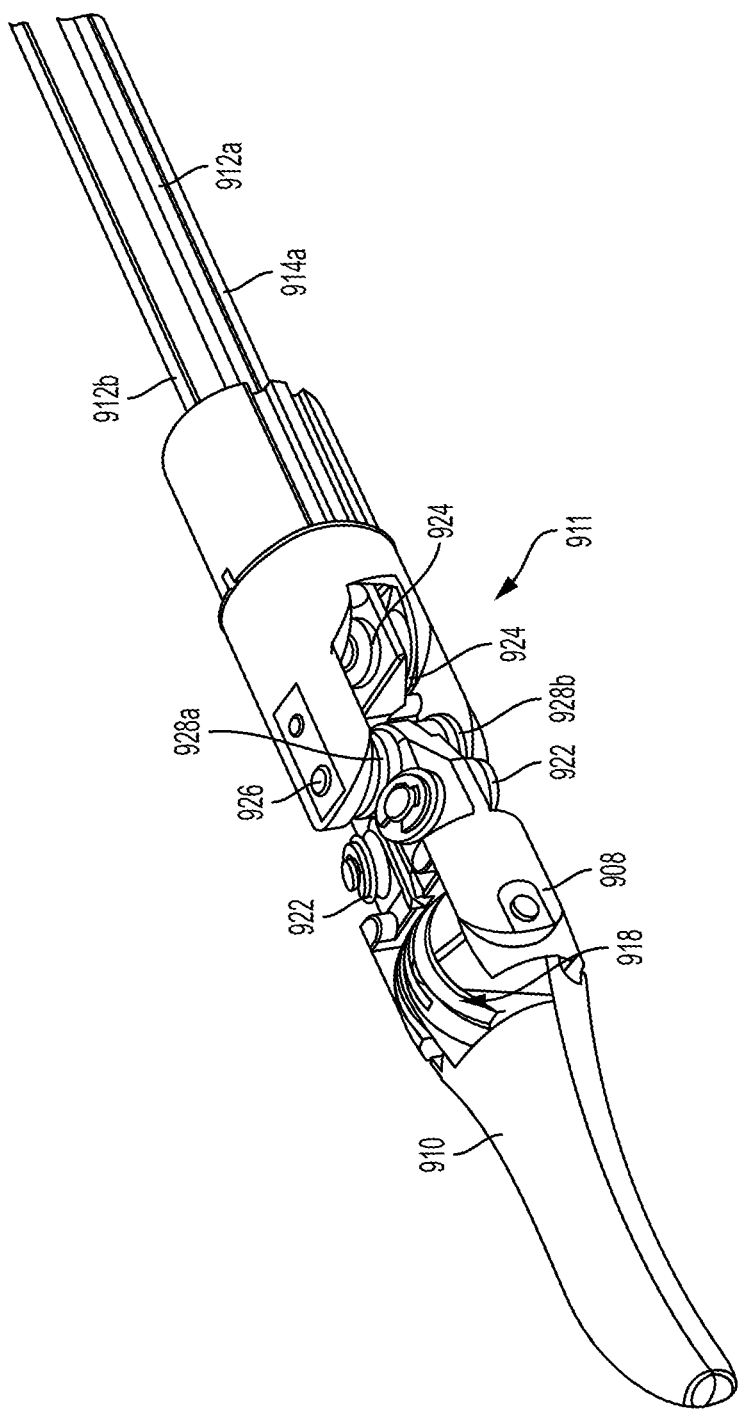
FIG. 44 is another perspective view of a distal portion of the surgical tool of FIG. 40.
Figure 45:
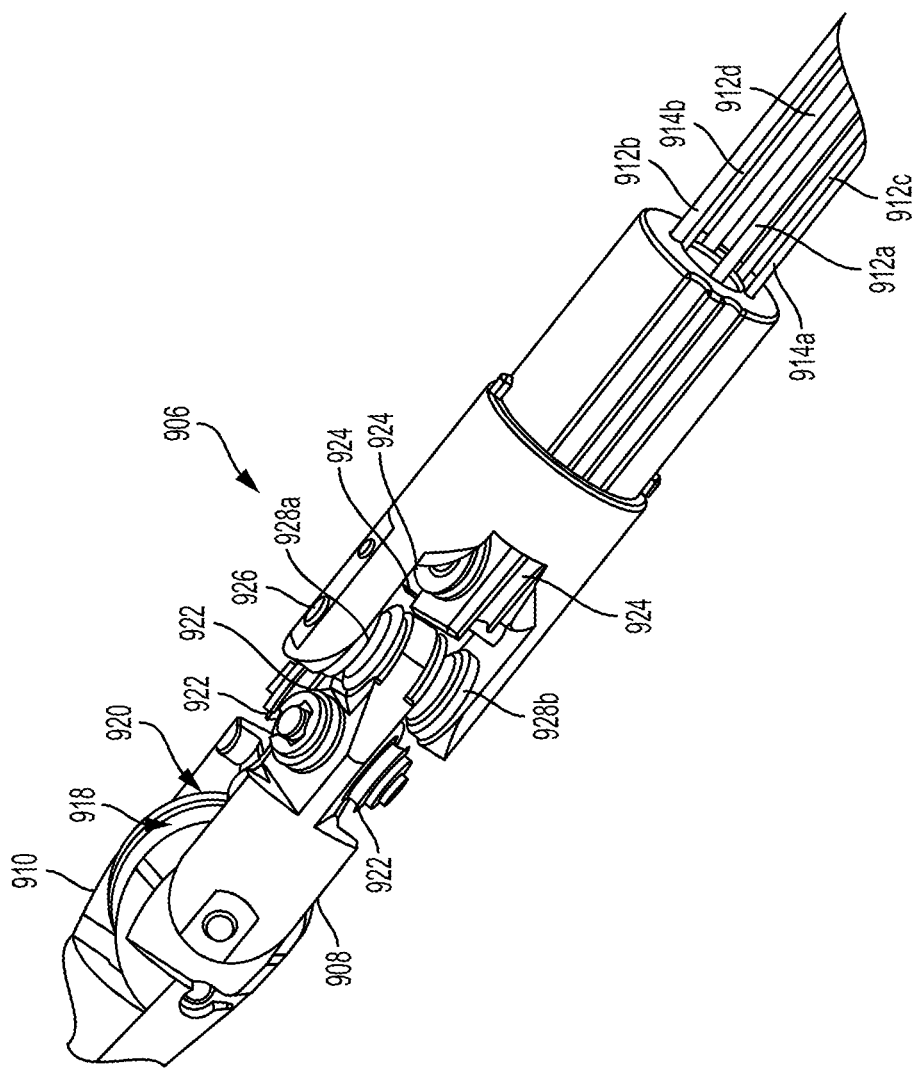
FIG. 45 is a perspective view of an intermediate portion of the surgical tool of FIG. 40.

As shown in FIGS. 43-45, the tool 900 includes a pair of grooves or channels 918, 920 at the end effector 904 that are each configured to seat one of the articulation and closure cables therein. One of the grooves 918 is formed in the bottom jaw 908, and the other groove 920 is formed in the upper jaw 910. In response to actuation of the cables, e.g., one of the cables being pulled proximally and the other of the cables being slacked, the end effector 904 will either open or close.

As also shown in FIGS. 43-45, the tool 900 includes a set of titled distal pulleys 922 and a set of titled proximal pulleys 924 each operatively associated with one of the tilted distal pullets 922. The pulleys 922, 924 are tilted with respect to a longitudinal axis 902A of the shaft 902. The four associated pairs of distal and proximal pulleys 922, 924 are each configured to be operatively engaged with one of the articulation and closure cables. One of the distal pulleys 922 and one of the proximal pulleys 924 is obscured in FIGS. 43-45. The titled orientation of the pulleys 922, 924 can allow the articulation and closure cables coupled thereto to extend substantially parallel to the shaft's longitudinal axis 902A but be radially offset therefrom, which may help reduce friction between the articulation and closure cables and their respective pulleys 922, 924 during articulation of the end effector 904. In response to actuation of a selected one of the articulation and closure cables, the end effector 904 can be selectively articulated in yaw movement about pivot point 926. The end effector 904 can be moved in the yaw direction by applying force to the cable which wraps around the end effector 904 in the desired direction of movement, for example to move to the left in the yaw direction, the cable which wraps around the lower jaw 908 can be pulled. The end effector 904 can be moved in the pitch direction by pitching the wrist 911 up and down with respect to a pin which connects the jaws 908, 910. The articulation and closure cables can rotate the jaws 908, 910 about this pin. Exemplary embodiments of pulleys configured to facilitate end effector articulation are further described in U.S. application Ser. No. 15/371,764 entitled "Surgical Tool Wrists" filed on Dec. 7, 2016, which is hereby incorporated by reference in its entirety.

As also shown in FIGS. 43-45, the tool 900 includes a pair of pulleys 928a, 928b that are each configured to operatively engage with one of the articulation and closure cables. The pulleys 928a, 928b are oriented substantially perpendicular to the shaft's longitudinal axis 902A.

Figure 46:
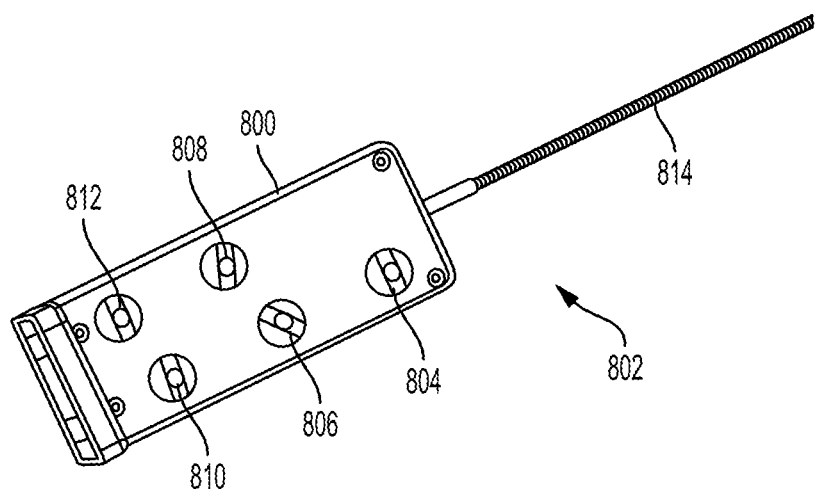
FIG. 46 is a perspective view of a proximal portion of another embodiment of a surgical tool.
Figure 47:
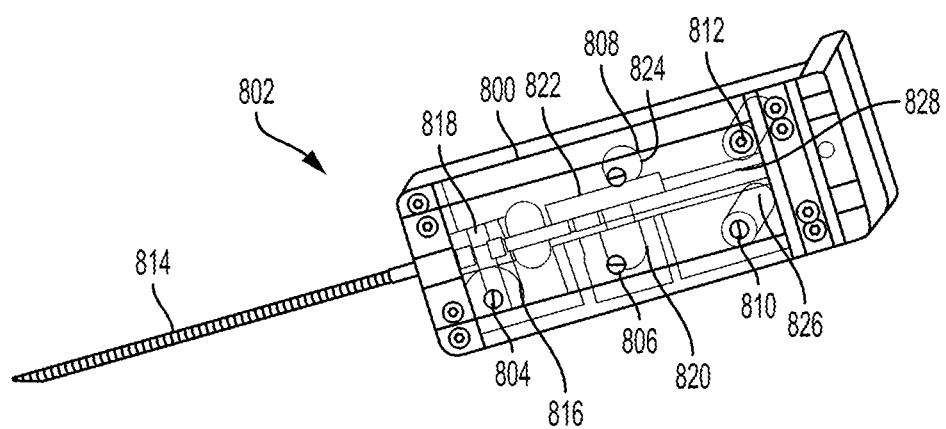
FIG. 47 is another perspective view of the proximal portion of the surgical tool of FIG. 46.

A surgical tool, such as the surgical tools configured to apply energy to tissue described herein, can include a tool housing configured to receive five inputs from a robotic surgical system coupled thereto to control end effector opening and closing, end effector articulation in pitch and yaw directions, cutting element movement (advancement and retraction), and elongate shaft rotation (which also rotates the end effector at the distal end of the shaft). FIGS. 46 and 47 illustrate one embodiment of a tool housing 800 of a surgical tool 802 having five input interfaces 804, 806, 808, 810, 812 each configured to receive an input from a robotic surgical system (e.g., a tool driver thereof) coupled to the tool housing 800. Only a proximal portion of the tool 802 is shown in FIGS. 46 and 47.

The first input interface 804 is configured to receive an input from the robotic surgical system to drive rotation of the elongate shaft 814 via a gear system. The input to the first input interface 804 is configured to cause rotation of a first gear 816. The input to the first input interface 804 can thus be a rotational input. The rotation of the first gear 816 is configured to rotate a second gear 818 operatively engaged therewith. The second gear 818 is operatively coupled to the shaft 814 such that rotation of the second gear 818 rotates the elongate shaft 814 (and the end effector at the distal end thereof).

The second input interface 806 is configured to receive an input from the robotic surgical system to drive selective end effector opening and closing via a rack and pinion system that is operatively coupled to the surgical tool's closure cable(s). The input to the second input interface 806 is configured to cause rotation of a pinion 820 that is operatively engaged with a rack (obscured in FIGS. 46 and 47). The input to the second input interface 806 can thus be a rotational input. The rotation of the pinion 820 is configured to cause longitudinal translation of the rack. The rack is operatively coupled with the closure cable(s) such that the translational movement of the rack causes corresponding translational movement of the closure cable(s), thereby effecting end effector opening (proximal translation, and rotation of the pinion 820 in one direction) or end effector closing (distal translation, and rotation of the pinion 820 in an opposite direction).

The third input interface 808 is configured to receive an input from the robotic surgical system to drive cutting element translation via a rack and pinion system that includes a rack 822 and a pinion 824 similar to the rack and pinion system for driving end effector opening and closing. The input to the third input interface 808 can thus be a rotational input. The rack 822 is operatively coupled with the tool's cutting element cable such that the translational movement of the rack 822 causes corresponding translational movement of the cutting element cable, thereby causing selective translation of the cutting element proximally (proximal translation of the rack 822, and rotation of the pinion 824 in one direction) or distally (distal translation of the rack 822, and rotation of the pinion 824 in an opposite direction).

The fourth input interface 810 is configured to receive an input from the robotic surgical system to drive two of the tool's four articulation cables, e.g., two left side articulation cables such as the left side articulation cables 226a, 226c of the tool 200 of FIGS. 6-8, to facilitate articulation of the end effector. The input to the fourth input interface 810 is configured to cause rotation of a gear 826 that in turn causes longitudinal translation of the two articulation cables operatively coupled thereto, such as via an articulation rod (obscured in FIGS. 46 and 47). The input to the fourth input interface 810 can thus be a rotational input.

The fifth input interface 812 is configured to receive an input from the robotic surgical system to drive the other two of the tool's four articulation cables, e.g., two right side articulation cables such as the right side articulation cables 226b, 226d of the tool 200 of FIGS. 6-8, to facilitate articulation of the end effector. The input to the fifth input interface 812 is configured to cause rotation of a gear 828 that in turn causes longitudinal translation of the two articulation cables operatively coupled thereto, such as via an articulation rod (obscured in FIGS. 46 and 47). The input to the fifth input interface 812 can thus be a rotational input.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 48:
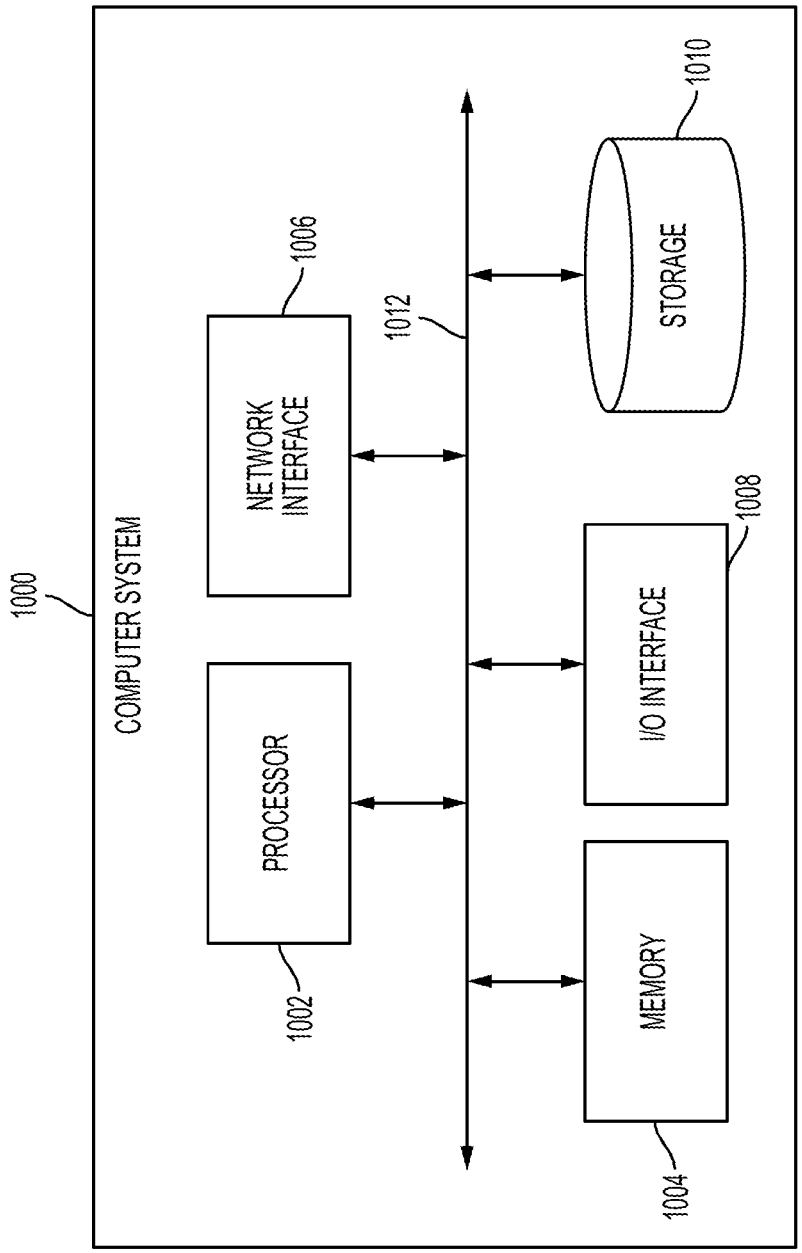
FIG. 48 is a schematic view of one embodiment of a computer system.

FIG. 48 illustrates one exemplary embodiment of a computer system 1000. As shown, the computer system 1000 includes one or more processors 1002 which can control the operation of the computer system 1000. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 1000 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1000 can be coupled to a bus system 1012. The illustrated bus system 1012 is an abstraction that represents any one or more separate physical busses, communication lines/interfaces, and/or multi-drop or point-to-point connections, connected by appropriate bridges, adapters, and/or controllers. The computer system 1000 can also include one or more network interface(s) 1006, one or more input/output (IO) interface(s) 1008, and one or more storage device(s) 1010.

The network interface(s) 1006 can enable the computer system 1000 to communicate with remote devices, e.g., other computer systems, over a network, and can be, for non-limiting example, remote desktop connection interfaces, Ethernet adapters, and/or other local area network (LAN) adapters. The IO interface(s) 1008 can include one or more interface components to connect the computer system 1000 with other electronic equipment. For non-limiting example, the IO interface(s) 1008 can include high speed data ports, such as universal serial bus (USB) ports, 1394 ports, Wi-Fi, Bluetooth, etc. Additionally, the computer system 1000 can be accessible to a human user, and thus the IO interface(s) 1008 can include displays, speakers, keyboards, pointing devices, and/or various other video, audio, or alphanumeric interfaces. The storage device(s) 1010 can include any conventional medium for storing data in a non-volatile and/or non-transient manner. The storage device(s) 1010 can thus hold data and/or instructions in a persistent state, i.e., the value(s) are retained despite interruption of power to the computer system 1000. The storage device(s) 1010 can include one or more hard disk drives, flash drives, USB drives, optical drives, various media cards, diskettes, compact discs, and/or any combination thereof and can be directly connected to the computer system 1000 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 48 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1000 can also include a web server for generating and/or delivering the web pages to client computer systems.

In an exemplary embodiment, the computer system 1000 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an elongate shaft;
an end effector configured to engage tissue, configured to apply energy to the tissue, and configured to selectively articulate at an angle relative to a longitudinal axis of the elongate shaft along a first plane and along a second plane that is transverse to the second plane, the end effector including a pair of jaws configured to move between open and closed positions;
a first cable and a second cable each extending along the elongate shaft offset from and substantially parallel to each other and the longitudinal axis of the elongate shaft, the first and second cables each being attached to one jaw of the pair of jaws, the first and second cables being configured to be actuated together to articulate the end effector in only yaw movement relative to the elongate shaft;
a third cable and a fourth cable each extending along the elongate shaft offset from and substantially parallel to each other and the longitudinal axis of the elongate shaft, the third and fourth cables each being attached to the one jaw of the pair of jaws, the third and fourth cables being configured to be actuated together to articulate the end effector in only pitch movement relative to the elongate shaft;
a fifth cable and a sixth cable each extending along the elongate shaft and substantially parallel to each other and the longitudinal axis of the elongate shaft, the fifth and sixth cables being configured to be actuated together to move the pair of jaws between the open and closed positions; and
a first link and a second link, each of the first and second links being pivotally attached to the jaw of the pair of jaws to which the first, second, third, and fourth cables are not attached, and the actuation of the fifth and sixth cables being configured to cause the first and second links to pivot to facilitate moving the pair of jaws between the open and closed positions;
wherein the end effector is at a distal end of the elongate shaft;
the fifth and sixth cables are configured to move proximally to cause the pair of jaws to move from the open position to the closed position;
the first and second links are configured to pivot in a proximal direction to cause the pair of jaws to move from the open position to the closed position;
the fifth and sixth cables are configured to move distally to cause the pair of jaws to move from the closed position to the open position; and
the first and second links are configured to pivot in a distal direction to cause the pair of jaws to move from the closed position to the open position.

2. The device of claim 1, wherein the first and second cables are configured to be actuated without the third and fourth cables being actuated such that the end effector articulates in only yaw movement, the third and fourth cables are configured to be actuated without the first and second cables being actuated such that the end effector articulates in only pitch movement, and the first, second, third and fourth cables are configured to be actuated together such that the end effector articulates in pitch movement and yaw movement.

3. The device of claim 1, further comprising a cutting element configured to move longitudinally along the end effector to cut tissue engaged by the end effector; and
a seventh cable extending along the elongate shaft and substantially parallel to the longitudinal axis of the elongate shaft, the seventh cable being configured to be actuated to cause the movement of the cutting element.

4. The device of claim 3, wherein the seventh cable is configured to be pushed distally to cause the movement of the cutting element.

5. The device of claim 3, wherein the seventh cable is operatively coupled to a pulley at a distal end of the end effector.

6. The device of claim 1, further comprising a single elongate linkage that is cannulated, the linkage being pivotally attached to the end effector at a first pivot joint and pivotally attached to the elongate shaft at a second pivot joint, wherein the second pivot joint is radially offset from the first pivot joint around a circumference of the linkage, and each of the first, second, third, and fourth cables extend along the linkage.

7. The device of claim 6, further comprising a tool housing, wherein the elongate shaft extends distally from the tool housing.

8. The device of claim 6, wherein:
a first channel is formed in a proximal end of the linkage and seats therein the first cable;
a second channel is formed in the proximal end of the linkage and seats therein the second cable;
a third channel is formed in the proximal end of the linkage and seats therein the third cable;
a fourth channel is formed in the proximal end of the linkage and seats therein the fourth cable;
a fifth channel is formed in a distal end of the linkage and seats therein the first cable;
a sixth channel is formed in the distal end of the linkage and seats therein the second cable;
a seventh channel is formed in the distal end of the linkage and seats therein the third cable; and
an eighth channel is formed in the distal end of the linkage and seats therein the fourth cable.

9. A surgical device, comprising:
a tool housing;
an elongate shaft extending distally from the tool housing;
an end effector configured to engage tissue, configured to apply energy to the tissue, and configured to selectively articulate at an angle relative to a longitudinal axis of the elongate shaft along a first plane and along a second plane that is transverse to the second plane, the end effector including a pair of jaws configured to move between open and closed positions;
a single elongate linkage that is cannulated and that is pivotally attached to the end effector at a first pivot joint and pivotally attached to the elongate shaft at a second pivot joint, the first pivot joint defining a first pivot axis, and the second pivot joint defining a second pivot axis that is substantially perpendicular to the first pivot axis;
a first cable and a second cable each extending along the elongate shaft offset from and substantially parallel to each other and the longitudinal axis of the elongate shaft, the first and second cables being configured to be actuated together to articulate the end effector at the first pivot joint about the first pivot axis in only yaw movement relative to the elongate shaft;
a third cable and a second cable each extending along the elongate shaft offset from and substantially parallel to each other and the longitudinal axis of the elongate shaft, the third and fourth cables being configured to be actuated together to articulate the end effector at the second pivot joint about the second pivot axis in only pitch movement relative to the elongate shaft;
a fifth cable and a sixth cable each extending along the elongate shaft and substantially parallel to each other and the longitudinal axis of the elongate shaft, the fifth and sixth cables being, configured to be actuated together to move the pair of jaws between the open and closed positions;
a first elongate link;
a second elongate link; and
a hub;
wherein a first end of each of the first and second elongate links is pivotally attached to one jaw of the pair of jaws at a third pivot joint, a second end of each of the first, and second elongate links is pivotally attached to the hub at a fourth pivot joint, and the actuation of the fifth and sixth cables is configured to cause the hub to translate longitudinally and thereby cause the first and second elongate links to pivot at the third and fourth pivot joints.

10. The device of claim 9, wherein the first, second, third, and fourth cables are each fixedly coupled to the end effector.

11. The device of claim 10, wherein the first and second cables are each fixedly coupled to one of the pair of jaws, and the third and fourth cables are each fixedly coupled to the one of the pair of jaws.

12. The device of claim 9, wherein a first channel is formed in a proximal end of the linkage and seats therein the first cable;
a second channel is formed in the proximal end of the linkage and seats therein the second cable;
a third channel is formed in the proximal end of the linkage and seats therein the third cable;
a fourth channel is formed in the proximal end of the linkage and seats therein the fourth cable;
a fifth channel is formed in a distal end of the linkage and seats therein the first cable;
a sixth channel is formed in the distal end of the linkage and seats therein the second cable;
a seventh channel is formed in the distal end of the linkage seats therein the third cable; and
an eighth channel is formed in the distal end of the linkage and seats therein the fourth cable.

13. The device of claim 9, wherein the first and second cables are configured to be actuated together without either of the third and fourth cables being actuated such that the end effector articulates in only yaw movement, the third and fourth cables are configured to be actuated together without either of the first and second cables being actuated such that the end effector articulates in only pitch movement, and the first, second, third, and fourth cables are configured to be actuated together such that the end effector articulates in pitch movement and yaw movement.

14. The device of claim 9, further comprising a cutting element configured to move longitudinally along the end effector to cut tissue engaged by the end effector; and
a fifth cable extending along the elongate shaft and substantially parallel to the longitudinal axis of the elongate shaft, the fifth cable being configured to be actuated to cause the movement of the cutting element.

15. The device of claim 14, wherein the fifth cable is configured to be pushed distally to cause the movement of the cutting element.

16. The device of claim 14, wherein the fifth cable is operatively coupled to a pulley at a distal end of the end effector.

* * * * *